United States Patent
Wang et al.

(10) Patent No.: US 11,427,633 B2
(45) Date of Patent: Aug. 30, 2022

(54) ANTI-CD19 HUMANIZED ANTIBODY AND IMMUNE EFFECTOR CELL TARGETING CD 19

(71) Applicant: CRAGE medical Co., Limited, Hong Kong (CN)

(72) Inventors: Peng Wang, Shanghai (CN); Huiping Gao, Shanghai (CN); Zhimin Shi, Shanghai (CN); Zonghai Li, Shanghai (CN)

(73) Assignee: CRAGE medical Co., Limited, Hong Kong (CN)

( * ) Notice: Subject to any disclaimer, the term of this patent is extended or adjusted under 35 U.S.C. 154(b) by 0 days.

(21) Appl. No.: 16/469,091

(22) PCT Filed: Dec. 13, 2017

(86) PCT No.: PCT/CN2017/115973
§ 371 (c)(1),
(2) Date: Jun. 12, 2019

(87) PCT Pub. No.: WO2018/108106
PCT Pub. Date: Jun. 21, 2018

(65) Prior Publication Data
US 2020/0062843 A1    Feb. 27, 2020

(30) Foreign Application Priority Data

Dec. 13, 2016  (CN) .......................... 201611148447.9

(51) Int. Cl.
| C07K 16/28 | (2006.01) |
| A61K 35/17 | (2015.01) |
| C07K 14/725 | (2006.01) |
| C12N 5/0783 | (2010.01) |
| C07K 14/705 | (2006.01) |
| A61K 38/00 | (2006.01) |

(52) U.S. Cl.
CPC .......... *C07K 16/2803* (2013.01); *A61K 35/17* (2013.01); *C07K 14/7051* (2013.01); *C07K 14/70517* (2013.01); *C07K 14/70521* (2013.01); *C07K 14/70578* (2013.01); *C07K 16/2809* (2013.01); *C12N 5/0636* (2013.01); *A61K 38/00* (2013.01); *C07K 2317/24* (2013.01); *C07K 2317/53* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01)

(58) Field of Classification Search
CPC ........ C07K 16/00–468; C07K 16/2803; C07K 2317/004; C07K 14/7051; A61K 35/17
See application file for complete search history.

(56) References Cited

U.S. PATENT DOCUMENTS

| 7,507,796 B2* | 3/2009 | Little | C07K 16/2809 |
| | | | 530/387.3 |
| 7,575,923 B2* | 8/2009 | Dorken | A61P 37/02 |
| | | | 435/328 |
| 7,902,338 B2* | 3/2011 | Hansen | A61K 45/06 |
| | | | 530/387.1 |
| 10,221,245 B2* | 3/2019 | Brogdon | A61P 35/02 |
| 2011/0206672 A1* | 8/2011 | Little | A61P 37/02 |
| | | | 424/136.1 |
| 2014/0112865 A1 | 4/2014 | Hansen et al. | |
| 2014/0271635 A1 | 9/2014 | Brogdon et al. | |
| 2016/0326249 A1* | 11/2016 | Ng | C07K 16/2809 |
| 2020/0261502 A1* | 8/2020 | Li | C12N 15/907 |

FOREIGN PATENT DOCUMENTS

| CN | 102209556 A | 10/2011 |
| CN | 105392888 A | 3/2016 |

OTHER PUBLICATIONS

Pezzutto et al., J. Immunol. 138:2793-99 (Year: 1987).*
Kochenderfer et al. Blood 116(20):4099-4102 (Year: 2010).*
Schindler et al. Brit J. Haematology 154: 471-476 (Year: 2011).*
Baeuerle et al. Cancer Res 69(12):4941-44 (Year: 2009).*
English Translation of the International Search Report dated Mar. 16, 2018 corresponding to PCT/CN2017/115973 filed Dec. 13, 2017; 3 pages.

* cited by examiner

*Primary Examiner* — Jessica H Roark
(74) *Attorney, Agent, or Firm* — Mintz, Levin, Cohn, Ferris, Glovsky and Popeo, P.C.

(57) ABSTRACT

Disclosed are an anti-CD19 humanized antibody prepared from a murine monoclonal antibody, a chimeric antigen receptor containing the humanized antibody, and an immune cell expressing the humanized antibody. Not only does the humanized antibody of the present invention not produce an anti-antibody response (AAR) and a human anti-mouse antibody response (HAMA), but same also has better affinity than a murine antibody, and has excellent activity and safety, thereby providing a new means for treating CD19-expressing tumors.

28 Claims, 8 Drawing Sheets
Specification includes a Sequence Listing.

ANTI-CD19 HUMANIZED ANTIBODY AND IMMUNE EFFECTOR CELL TARGETING CD19

TECHNICAL FIELD

The present invention belongs to the field of immunotherapy or diagnosis of tumors. In particular, the present invention relates to humanized antibodies against CD19 and immune effector cells that target CD19.

REFERENCE TO A "SEQUENCE LISTING,"

The Sequence_Listing.txt, created on Jun. 18, 2021 (42,693 bytes in size), machine format IBM-PC, MS-Windows operating system, is hereby incorporated by reference in its entirety for all purposes.

BACKGROUND

B cells include pre-B cells, early-developed B cells (i.e., immature B cells) and mature B cells, and mature B cells differentiate into plasma cells and malignant B cells through terminal differentiation. CD19 is highly expressed in most pre-B acute lymphoblastic leukemia (ALL), non-Hodgkin's malignant lymphoma, B-cell chronic lymphocytic leukemia (CLL), pro-lymphocytic leukemia, hairy cell leukemia, common acute lymphocytic leukemia some non-acute lymphoblastic leukemias (Nadler et al, J. Immunol., 131: 244-250 (1983); Loken et al, Blood, 70: 1316-1324 (1987)). The expression of CD19 on plasma cells further indicates that it can be expressed on different B cell tumors such as multiple myeloma, plasmacytoma, and phylloblastoma (Grossbard et al, Br. J. Haematol, 102: 509-15 (1998); Treon et al, Semin. Oncol, 30: 248-52 (2003)). Therefore, CD19 is considered as a target for a variety of blood tumors.

Current antibodies against CD19 are mainly murine antibodies, such as mouse anti-HD37 disclosed in J Immunol. 1987 May 1; 138(9): 2793-9, Blinatumomab marketed by Amgen. However, murine antibodies have strong immunogenicity and can cause human anti-mouse antibody (HAMA) reaction and anti-antibody reaction (AAR) in clinical applications, resulting in shortened half-life, prone to be cleared, weak therapeutic effect, and serious threat to patients' life.

A commonly used method for reducing the immunogenicity of murine antibody is humanization, by for example replacing the murine framework region with human framework region to reduce the immunological side effects of the heterologous antibody on the human body. For example, CN102209556A disclosed a humanized antibody of murine antibody HD37 and disclosed that when phenylalanine was used to place serine at position 91 of VH (heavy chain variable region), the expression level will be increased.

Since there are many humanized framework regions, it is technically difficult for humanization to screen appropriate framework regions, express human antibodies and maintain binding abilities of antibodies after humanization. In particular, after humanization of an antibody, changes in the amino acid sequence usually change the size, charge, hydrophobicity and spatial conformation of the peptide chain, and the formation of hydrogen bonds is different from that of the murine antibody, thereby affecting the conformation of complementarity determining region (CDR) of the antibody. Therefore, after humanization, the affinity, specificity and the like of an antibody are generally reduced by more than 10-fold compared with the murine antibody (Vahideh Ahmadzadeh et al, Monoclonal antibodies in immunodiagnosis and immunotherapy, volume 33, number 2, 2014).

Therefore, there is an urgent need in the art for humanized antibodies which can have the same, even higher affinity, as compared with the murine antibodies, and do not produce anti-antibody reaction (AAR) and human anti-mouse antibody (HAMA) reaction, thereby providing higher security.

SUMMARY OF THE INVENTION

It is an object of the present invention to provide a humanized antibody against CD19 and an immune effector cell targeting CD19.

In a first aspect, a humanized antibody against human CD19 having a binding relative affinity ($EC_{50}$) of less than 10 nM to K562 cells stably transfected with human CD19 is provided in the present invention.

In a preferred embodiment, the humanized antibody has a binding relative affinity (EC50) between 1-10 nM to K562 cells stably transfected with human CD19.

In a specific embodiment, the framework regions of the light chain variable region of the humanized antibody are shown in 1-23, 39-53, 61-92 and 102-111 of SEQ ID NO: 1; and/or the framework regions of the heavy chain variable region of the humanized antibody are shown in 1-30, 36-49, 67-98 and 114-124 of SEQ ID NO: 3.

In a specific embodiment, the antibody is selected from a group consisting of:

(a) an antibody having a light chain variable region of SEQ ID NO: 1 or a variant thereof;

(b) an antibody having a heavy chain variable region of SEQ ID NO: 3 or a variant thereof;

(c) an antibody having the light chain variable region of the antibody of (a) and the heavy chain variable region of the antibody of (b); and (d) an antibody which is a humanized antibody competing with the antibody of any one of (a) to (c) for binding to human CD19.

In a specific embodiment, the variant in (a) has LCDR1 as shown in SEQ ID NO: 17, LCDR2 as shown in SEQ ID NO: 13 and LCDR3 as shown in SEQ ID NO: 14.

In a specific embodiment, the variant of (a) has the light chain variable region as shown in SEQ ID NO:7.

In a specific embodiment, the variant of (b) has HCDR1 as shown in SEQ ID NO: 15, HCDR2 as shown in SEQ ID NO: 16 and HCDR3 as shown in SEQ ID NO: 11.

In a specific embodiment, the variant of the antibody of (b) has the heavy chain variable region as shown in SEQ ID NO: 5.

In a specific embodiment, the humanized antibody is selected from a group consisting of:

(a) an antibody having the light chain variable region of SEQ ID NO: 1 and the heavy chain variable region of SEQ ID NO: 3;

(b) an antibody having the light chain variable region of SEQ ID NO: 1 and the heavy chain variable region of SEQ ID NO: 5;

(c) an antibody having the light chain variable region of SEQ ID NO: 7 and the heavy chain variable region of SEQ ID NO: 3; and (d) an antibody having the light chain variable region of SEQ ID NO: 7 and the heavy chain variable region of SEQ ID NO: 5.

In a preferred embodiment, phenylalanine is not present at position 91 of the heavy chain variable region of the humanized antibody.

In a second aspect, a nucleotide sequence is provided in the present invention, encoding the antibody of the first aspect of the present invention.

In a third aspect, an expression vector is provided in the present invention, comprising the nucleotide sequence of the second aspect of the present invention.

In a fourth aspect, a host cell is provided in the present invention, comprising an expression vector of the third aspect of the present invention or having a nucleotide sequence according to the second aspect of the present invention integrated into its genome.

In a fifth aspect, a use of the humanized antibody of the first aspect of the present invention is provided in the present invention for the preparation of a targeted drug, antibody drug conjugate or multifunctional antibody which specifically targets tumor cells expressing CD19; or for the preparation of an agent that diagnoses a tumor expressing CD19; or for the preparation of a chimeric antigen receptor-modified immune cell.

In a sixth aspect, a chimeric antigen receptor is provided in the present invention, comprising an extracellular domain, a transmembrane domain and an intracellular signal domain, wherein the extracellular domain comprises an antibody of the first aspect of the invention, preferably a single chain antibody or domain antibody.

In a specific embodiment, the intracellular signal domain comprises one or more co-stimulatory signal domains and primary signal domains.

In a specific embodiment, the chimeric antigen receptor further comprises a hinge domain.

In a specific embodiment, the transmembrane domain is selected from the group consisting of transmembrane region of alpha, beta, zeta chain of TCR, CD3ε, CD3ζ, CD4, CD5, CD8α, CD9, CD16, CD22, CD27, CD28, CD33, CD37, CD45, CD64, CD80, CD86, CD134, CD137, CD152, CD154 and PD1; and/or the co-stimulatory signal domain is selected from the group consisting of the intracellular signal region of CARD11, CD2, CD7, CD27, CD28, CD30, CD40, CD54, CD83, OX40, CD137, CD134, CD150, CD152, CD223, CD270, PD-L2, PD-L1, CD278, DAP10, LAT, NKD2C SLP76, TRIM, FcεRIγ, MyD88 and 41BBL; and/or the primary signal domain is selected from the group consisting of TCR ξ, FcR γ, FcR β, CD3 γ, CD3δ, CD3ε, CD5, CD22, CD79a, CD79b, CD278 (also referred to as "ICOS"), CD66d and CD3ζ;

preferably, the transmembrane domain is selected from the group consisting of the transmembrane domain of CD8α, CD4, CD45, PD1, CD154 and CD28; and/or the co-stimulatory signal domain is selected from the group consisting of CD137, CD134, CD28 and OX40; and/or the primary signal domain is selected from the group consisting of CD3ζ, most preferably, the transmembrane domain is selected from the group consisting of CD8α or CD28, the co-stimulatory signal domain is selected from the intracellular signal domain of CD137 or CD28, and the primary signal domain is selected from the group consisting of CD3ζ.

In a specific embodiment, the chimeric antigen receptor comprises the following sequentially linked antibody, transmembrane region and intracellular signal region:

an antibody of the first aspect of the present invention, CD8 and CD3ζ;

an antibody of the first aspect of the present invention, CD8, CD137 and CD3ζ;

an antibody of the first aspect of the present invention, the transmembrane region of CD28 molecule, the intracellular signal region of CD28 molecule and CD3ζ; or an antibody of the first aspect of the present invention, the transmembrane region of CD28 molecule, the intracellular signal region of CD28 molecule, CD137 and CD3ζ.

In a specific embodiment, the extracellular domain has the amino acid sequence of SEQ ID NO: 21;

the transmembrane domain is selected from the group consisting of the transmembrane domain of CD28 as shown in SEQ ID NO: 27, and the transmembrane domain of CD8 as shown in SEQ ID NO: 33;

the co-stimulatory signal domain is selected from the group consisting of the intracellular domain of CD28 as shown in SEQ ID NO: 29 and the intracellular domain of CD137 as shown in SEQ ID NO: 35, or a mixture thereof.

In a specific embodiment, the chimeric antigen receptor is selected from the group consisting of:

chimeric antigen receptor I, which has an extracellular domain as shown in SEQ ID NO: 21, a hinge domain as shown in SEQ ID NO: 25, a transmembrane domain as shown in SEQ ID NO: 27, a co-stimulatory signal domain as shown in SEQ ID NO: 29 and a primary signal domain as shown in SEQ ID NO: 31 (huHD37-28Z);

chimeric antigen receptor II, which has an extracellular domain as shown in SEQ ID NO: 21, a hinge domain as shown in SEQ ID NO: 25, a transmembrane domain as shown in SEQ ID NO: 33, a co-stimulatory signal domain as shown in SEQ ID NO: 35 and a primary signal domain as shown in SEQ ID NO: 31 (huHD37-BBZ); or chimeric antigen receptor III, which has an extracellular domain as shown in SEQ ID NO: 21, a hinge domain as shown in SEQ ID NO: 25, a transmembrane domain as shown in SEQ ID NO: 27, a costimulatory signal domain as shown in SEQ ID NO: 29 and SEQ ID NO: 35 and a primary signal domain as shown in SEQ ID NO: 31 (huHD37-28BBZ).

In a seventh aspect, a nucleotide sequence is provided in the present invention, encoding a chimeric antigen receptor of the sixth aspect of the present invention.

In an eighth aspect, an expression vector is provided in the present invention, comprising the nucleotide sequence of the seventh aspect of the present invention.

In a ninth aspect, a virus is provided in the present invention, comprising the expression vector of the eighth aspect of the present invention.

In a tenth aspect, a use of the chimeric antigen receptor of the sixth aspect, or the nucleotide sequence of the seventh aspect, or the expression vector of the eighth aspect, or the virus of the ninth aspect of the present invention for preparing genetically modified immune cells that target CD19-expressing tumor cells is provided in the present invention.

In an eleventh aspect, a genetically modified immune cell is provided in the present invention, which is transduced with the nucleotide sequence of the seventh aspect of the present invention, or the expression vector of the eighth aspect of the present invention or the virus of the ninth aspect of the present invention; or expresses the chimeric antigen receptor of the sixth aspect of the present invention.

In a specific embodiment, the genetically modified immune cell of the present invention further expresses a sequence other than a chimeric antigen receptor, wherein the other sequence comprises a cytokine, another chimeric antigen receptor, a chemokine receptor, an siRNA that reduces expression of PD-1 or a protein that blocks PD-L1, TCR, or a safety switch;

preferably, the cytokine comprises IL-12, IL-15, IL-21 or type I interferon;

preferably, the chemokine receptor comprises CCR2, CCR5, CXCR2 or CXCR4;

preferably, the safety switch comprises iCaspase-9, Truncated EGFR or RQR8.

In a twelfth aspect, a use of the genetically modified immune cell of the eleventh aspect of the present invention is provided in the present invention, for preparing a medicament for inhibiting tumors expressing CD19.

In a thirteenth aspect, a multifunctional immunoconjugate is provided in the present invention, comprising:

an antibody of the first aspect of the present invention;

a functional molecule linked thereto, wherein the functional molecule is selected from the group consisting of a molecule that targets other tumor surface markers other than CD19, a molecule that inhibits tumors, a molecule that targets a surface marker on an immune cell, or a detectable label.

In a specific embodiment, the molecule that targets a tumor surface marker is an antibody or ligand that binds to the tumor surface marker; or the molecule that inhibits tumor is an antitumor cytokine or an antitumor toxin; preferably, the cytokine comprises: IL-12, IL-15, IFN-beta, TNF-alpha.

In a preferred embodiment, the detectable label comprises: a fluorescent label, a chromogenic label.

In a specific embodiment, the molecule that targets a surface marker of an immune cell is an antibody that binds to a T cell surface marker, and forms a bifunctional antibody involving T cell with the antibody of the first aspect of the present invention; and preferably, the antibody that binds to a T cell surface marker is an anti-CD3 antibody.

In a specific embodiment, the multifunctional immunoconjugate of the present invention is a fusion polypeptide, and a linker peptide is further included between the antibody of the first aspect of the present invention and a functional molecule linked thereto.

In a fourteenth aspect, a nucleotide sequence encoding the multifunctional immunoconjugate of the thirteenth aspect of the present invention is further provided in the present invention.

In a fifteenth aspect, a use of the multifunctional immunoconjugate of the thirteenth aspect of the present invention is provided in the present invention for preparing an antitumor drug, or preparing an agent that diagnoses a tumor expressing CD19; or preparing a chimeric antigen receptor-modified immune cell.

In a sixteenth aspect, a pharmaceutical composition is provided in the present invention, comprising:

an antibody according to the first aspect of the present invention or a nucleotide sequence encoding the antibody; or a chimeric antigen receptor according to the sixth aspect of the present invention, or a nucleotide sequence encoding the chimeric antigen receptor; or a genetically modified immune cell of the eleventh aspect of the present invention; or a immunoconjugate of the thirteenth aspect of the present invention or a nucleotide sequence encoding the conjugate.

It is to be understood that within the scope of the present invention, the various technical features of the present invention and the technical features specifically described hereinafter (as in the embodiments) may be combined with each other to constitute a new or preferred technical solution, which will not be repeated herein one by one.

DESCRIPTION OF FIGURES

FIG. 1 compares amino acid sequences of HD37, human antibody variable region, human antibody variable region/ligation region, and humanized antibody huHD37 (SEQ ID Nos: 49-56).

FIG. 6 compares the amino acid sequences of 6B3, 8E3 and the humanized antibody huHD37 (SEQ ID Nos:3, 5 and 20 and SEQ ID Nos:1, 19 and 7);

MODE FOR CARRYING OUT THE INVENTION

Figure 2:
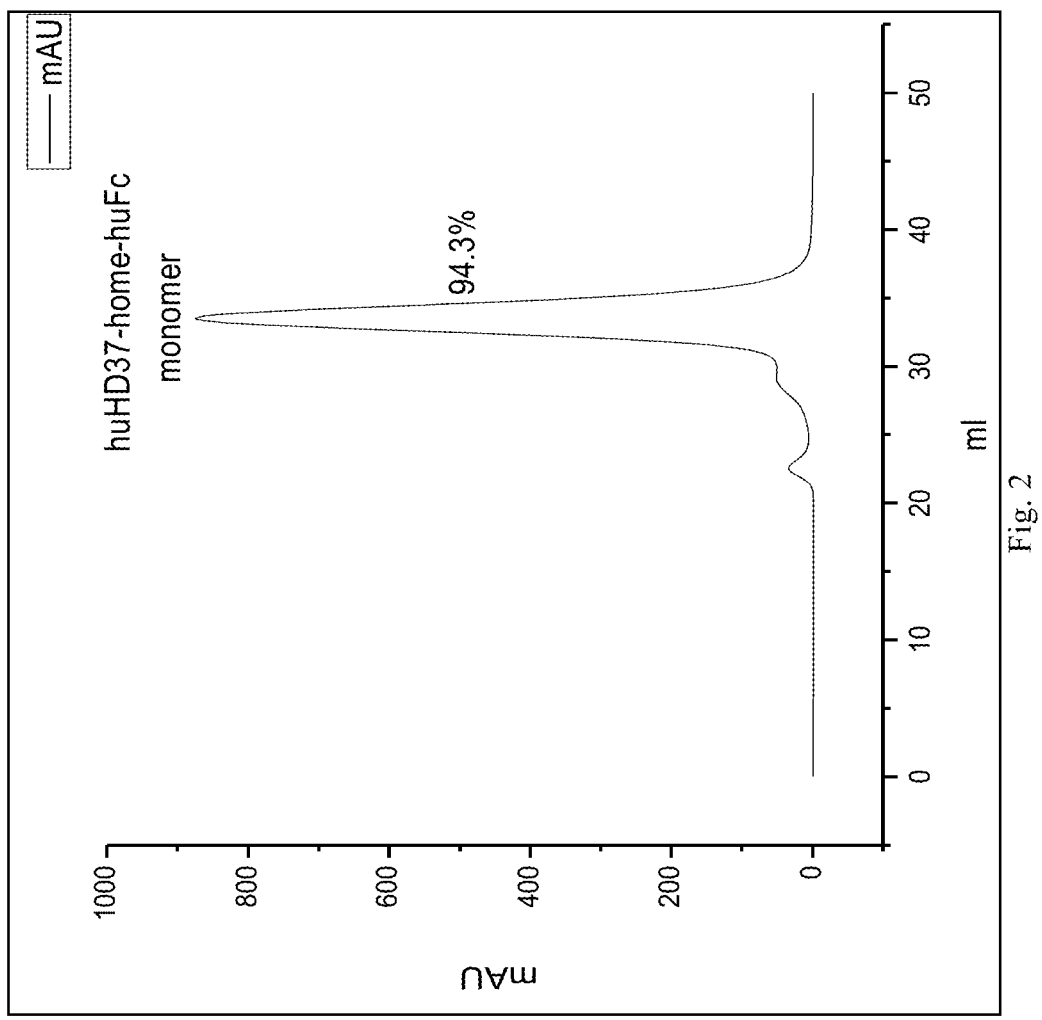
FIG. 2 shows SEC analysis on the aggregation of huHD37 (ScFv_Fc)

Through extensive and intensive research, the inventors have unexpectedly discovered that a humanized antibody binding to CD19 prepared from a murine monoclonal antibody according to the present invention does not produce an anti-antibody reaction (AAR) and a human anti-mouse antibody reaction (HAMA) and exhibits a better affinity than mouse antibody, thereby possessing excellent activity and safety. The present invention was completed based on the above findings.

For clearly understanding the present invention, some terms are first defined.

The term "CD19" includes, but is not limited to, variants, isoforms and species homologs of human CD19. In certain instances, the humanized antibody of the invention can cross-react with CD19 of a species other than human. In certain instances, the antibody may be completely specific to one or more human CD19 proteins and may exhibit non-human cross-reactivities of species or other types. The complete amino acid sequence of an exemplary human CD19 can be found in SwissPort Accession No. P15391 (SEQ ID NO: 18). CD19 is also known as B cell surface antigen B4, B cell antigen CD19, CD19 antigen or Leu-12. Human CD19 is named as Gene ID: 930 in Entrez Gene and HGNC: 1633 in HGNC. CD19 can be encoded by CD19 gene. "Human CD19" is used herein to encompass all known or still undiscovered alleles and polymorphic forms of human CD19.

The term "antibody" can be an intact immunoglobulin molecule comprising at least two heavy (H) chains and two light (L) chain glycoproteins interconnected by disulfide bonds. The term "antibody" also includes all recombinant forms of an antibody, particularly the antibody described herein, such as an antibody expressed in prokaryotic cells, an unglycosylated antibody, as well as antibody fragments that bind to antigens and derivatives described hereinafter. Each heavy chain consists of a heavy chain variable region (abbreviated herein as VH) and a heavy chain constant region. Each light chain consists of a light chain variable region (abbreviated herein as VL) and a light chain constant region. VH and VL include complementarity determining regions (CDR) and framework regions (FR). Each VH and VL consists of three CDRs and four FRs, arranged from the amino terminus to the carboxy terminus in the following order: FR1, CDR1, FR2, CDR2, FR3, CDR3, FR4. The variable regions of the heavy and light chains contain binding domains that interact with an antigen. The constant region of the antibody can mediate binding of the immunoglobulin to host tissues or factors, including various cells of the immune system (such as effector cells) and the first component (C1q) of the classical complement system.

The term "antibody" may also be an antigen-binding fragment, including but not limited to Fab fragment, Fd fragment, Fv fragment, F(ab')2 fragment, single chain antibody (scFv), domain antibody, bivalent single chain antibody, single chain phage antibody, bispecific di-chain antibody, tri-chain antibody, or four-chain antibody. Since an antibody can be modified in a variety of modes, the term "antibody" is understood to further include any polypeptide or protein having an antibody binding domain or a binding domain homologous thereto. The term "Fab" includes polypeptides comprising VH, CH1, VL and CL immunoglobulin domains.

The term "recombinant antibody" as used herein includes all antibodies prepared, expressed, produced or isolated by recombinant means, such as (a) an antibody isolated in an animal (e.g, a mouse) in which the immunoglobulin gene is a transgene or a transchromosome, or in a hybridoma prepared therefrom, (b) an antibody isolated from a host cell transformed to express an antibody (such as a transfectoma), (c) an antibody isolated from a recombinant combinatorial antibody library, and (d) an antibody prepared, expressed, produced or isolated by any other means involving splicing the immunoglobulin gene sequence into a DNA sequence.

The term "humanized antibody" as used herein refers to an antibody in which CDR sequences derived from a germline of another mammalian species (e.g., a mouse) is transplanted into human framework sequence. In human framework sequences and CDR sequences derived from a germline of another mammalian species, additional modifications on framework region can also be made.

If the variable framework region of an antibody is obtained from a system using a human germline immunoglobulin gene, the humanized antibody used herein includes a heavy or light chain variable framework region, which is a "product" of a specific human germline sequence (human gene) or "derived from" the specific human germline sequence. Such system includes a transgenic mouse carrying a human immunoglobulin gene immunized with a target antigen, or a human immunoglobulin gene library displayed on a phage screened with a target antigen. The amino acid sequence of the heavy or light chain variable framework region of a humanized antibody can be compared with the amino acid sequence of the heavy or light chain variable framework region of a human germline immunoglobulin for identifying a humanized antibody comprising the heavy chain or light chain variable framework region, wherein the variable framework region is a "product" of a human germline immunoglobulin sequence or "derived from" the human germline immunoglobulin sequence. A humanized antibody comprising a heavy or light chain variable framework region that is a "product" of a specific human germline immunoglobulin sequence has a heavy or light chain variable frame region, the amino acid sequence of which is 100% identical to that of the heavy or light chain variable framework region of the specific human germline immunoglobulin sequence. Compared with the heavy or light chain variable framework region of a specific germline sequence, a humanized antibody comprising the heavy or light chain variable framework region "derived from" the specific human germline immunoglobulin sequence may contain amino acid differences due to, for example, naturally occurring somatic mutations or intentionally introduced site-directed mutagenesis. However, typically the amino acid sequence of the heavy or light chain variable framework region of a selected humanized antibody is at least 90% identical to the amino acid sequence encoded by the heavy or light chain variable framework region of the human germline immunoglobulin gene, and, when compared with the amino acid sequence of germline immunoglobulin of other species (e.g., a murine germline sequence), the amino acid residues of the identified humanized antibody are those derived from humans. In certain instances, the amino acid sequence of the heavy or light chain variable framework region of the humanized antibody are preferably at least 95%, more preferably at least 96%, most preferably at least 97%, especially at least 98% and at least 99% identical to the amino acid sequence of the heavy or light chain variable framework region encoded by the germline immunoglobulin gene. Typically, the heavy or light chain variable framework region of a humanized antibody derived from a specific human germline sequence will exhibit no more than 10, preferably no more than 5, or even more preferably no more than 4, 3, 2 or 1 amino acid difference from the heavy or light chain variable framework region encoded by a human germline immunoglobulin gene.

The term "parent antibody" includes a murine antibody or humanized antibody to be modified to produce other humanized antibodies.

The term "variant" as used herein includes an antibody sequence that differs from the parent antibody sequence by at least one amino acid modification compared with the parent antibody. In a specific embodiment, a variant antibody sequence herein has at least about 80%, preferably at least about 90%, more preferably at least about 95%, more preferably at least about 97%, more preferably at least about 98%, most preferably at least about 99% amino acid sequence identity to the parent antibody sequence. An antibody variant can refer to the antibody itself, a composition comprising the parent antibody, or a nucleotide sequence encoding the same. The term "amino acid modification" includes amino acid substitution, addition and/or deletion, and "amino acid substitution" refers to the replacement of an amino acid at a particular position in a parent polypeptide sequence with another amino acid. For example, substitution R94K means that the arginine at position 94 is replaced by lysine, and "amino acid insertion" as used herein refers to the addition of an amino acid at a particular position in a parent polypeptide sequence. As used herein, "amino acid deletion" or "deletion" refers to removal of an amino acid at a particular position in a parent polypeptide sequence.

The term "conservative modification" or "conservative sequence modification" as used herein refers to an amino acid modification that does not significantly affect or alter the binding characteristics of an antibody comprising the amino acid sequence. Such conservative modifications include amino acid substitutions, insertions, and deletions. Modifications can be introduced into the antibodies of the invention by standard techniques known in the art, such as site-directed mutagenesis and PCR-mediated mutagenesis. Conservative amino acid substitutions are substitutions in which amino acid residues are replaced with amino acid residues having similar side chains. A family of amino acid residues having similar side chains has been defined in the art. These families include amino acids containing basic side chains (e.g., lysine, arginine, histidine), acidic side chains (e.g., aspartic acid, glutamic acid), uncharged acute side chains (e.g., glycine, asparagine, serine, threonine, tyrosine, cysteine, tryptophan), non-polar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Therefore, one or more amino acid residues in the CDR regions or the framework regions of the antibody of the present invention can be replaced with amino acid residues of other families with identical side chain, and the function retained by the altered antibody (variant antibody) can be tested.

The term "ADCC" or "antibody-dependent cell-mediated cytotoxicity" as used herein includes cell-mediated responses in which a non-specific cytotoxic cell expressing FcγR recognizes an antibody bound on a target cell, thereby causing target cell lysis. In various aspects, enhancing ADCC effector function can refer to enhanced potency or enhanced efficacy. The "potency" used in the experiment refers to the concentration of an antibody (half maximal effective concentration) when the specific therapeutic efficacy EC50 is observed. "Efficacy" as used in the experiment refers to the maximum possible effector function of an antibody at saturation levels.

The term "ADCP" or "antibody-dependent cell-mediated phagocytosis" as used herein includes cell-mediated responses in which non-specific cytotoxic cells expressing FcγR recognize an antibody bound to target cells, thereby causing phagocytosis of target cells.

The term "CDC" or "complement dependent cytotoxicity" as used herein includes a reaction in which one or more complement protein components recognize an antibody bound on a target cell, followed by lysis of the target cell.

The term "effector function" as used herein includes biochemical events resulting from the interaction of an antibody Fc region with an Fc receptor or ligand. Effector functions include FcγR-mediated effector functions such as ADCC and ADCP, and complement-mediated effector functions such as CDC.

The term "chimeric antigen receptor" or "CAR" as used herein, refers to a polypeptide comprising an extracellular domain capable of binding an antigen, a transmembrane domain, and a cytoplasmic signaling domain (i.e., an intracellular signal domain), and the intracellular signal domain refers to a protein that transmits signals into a cell by producing a second messenger through a defined signaling pathway, thereby regulating cellular activities, or a protein that corresponds to such a messenger and acts as an effector, including a primary signal domain and a functional signaling domain (i.e., a co-stimulatory signal domain) derived from a stimulatory molecule as defined below. The intracellular signal domain produces a signal that promotes the immune effector function of cells of the CAR (e.g., CAR T cells), and examples of immune effector functions, such as in CART cells, includes cell lytic activity and helper activity, including secretion of cytokine.

The term "primary signal domain" refers to modulating the initial activation of a TCR complex in an irritating manner. In one aspect, the primary signal domain is elicited by, for example, binding of a TCR/CD3 complex to a peptide-loaded MHC molecule, thereby mediating a T cell response (including, but not limited to, proliferation, activation, differentiation, etc.). The primary signal domain that functions in a stimulatory manner may comprise an immunoreceptor tyrosine activation motif or a signaling motif of ITAM. Examples of primary signal domains comprising ITAM that are particularly useful in the present invention include, but are not limited to, the sequence derived from TCR ξ, FcRγ, FcRβ, CD3γ, CD3δ, CD3ε, CD5, CD22, CD79a, CD79b, CD278 (also referred to as "ICOS") and CD66d. In an exemplary CAR of the invention, in any one or more of the CARs of the invention, the intracellular signaling domain comprises an intracellular signaling sequence, such as the primary signal domain of CD3ξ.

The term "co-stimulatory signal domain" refers to a "co-stimulatory molecule" which is a related binding partner on a T cell that specifically binds to a co-stimulatory ligand, thereby mediating a co-stimulatory response of a T cell, such as, but not limited to, proliferation. Co-stimulatory molecules are cell surface molecules or ligands thereof which are required for an effective immune response and non-antigen receptors. Co-stimulatory molecules include, but are not limited to, MHC class I molecules, BTLA and Toll ligand receptors, as well as OX40, CD2, CD27, CD28, CDS, ICAM-1, LFA-1 (CD11a/CD18) and 4-1BB (CD137).

In the present invention, in one aspect, the CAR comprises a chimeric fusion protein comprising an extracellular antigen recognition domain, a transmembrane domain and an intracellular signaling domain, and the intracellular signaling domain comprises a functional signaling domain derived from a stimulatory molecule. In one aspect, the CAR comprises a chimeric fusion protein comprising an extracellular antigen recognition domain, a transmembrane domain and an intracellular signaling domain, and the intracellular signaling domain comprises a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain, and the intracellular signaling domain comprises at least two functional signaling domains derived from one or more co-stimulatory molecules and a functional signaling domain derived from a stimulatory molecule. In one aspect, the CAR comprises an optional leader sequence at the amino acid (ND end) of the CAR fusion protein. In one aspect, the CAR further comprises a leader sequence at N-terminus of the extracellular antigen recognition domain, wherein the leader sequence is optionally cleaved from the antigen recognition domain (e.g., scFv) during processing and localization of the CAR to the cell membrane.

The term "CD3ξ" as used herein is defined as a protein provided by GenBan Accession No. BAG36664.1, or equivalent residues from a non-human species such as a mouse, rodent, monkey, ape, and the like. "CD3ξ domain" as used herein is defined as amino acid residues from the cytoplasmic domain of ξ chain sufficient to functionally deliver the initial signal required for T cell activation. In one aspect, the cytoplasmic domain of ξ comprises residues 52 to 164 of GenBan Accession No. BAG36664.1, a functional ortholog thereof—equivalent residues from non-human species such as a mouse, rodents, monkey, ape, etc.

The term "4-1BB" as used herein refers to a member of TNFR superfamily having the amino acid sequence of GenBank Acc. No. AAA62478.2, or equivalent residues from a non-human species such as a mouse, rodent, monkey, ape and the like. "4-1BB co-stimulatory domain" is defined as amino acid sequence 214-255 of GenBank ACC. No. AAA62478.2, or equivalent residues from non-classified species such as mouse, rodent, monkey, ape, etc. In one aspect, the "4-1BB co-stimulatory domain" is the sequence provided in SEQ ID NO: 35, or equivalent residues from a non-human species such as a mouse, rodent, monkey, ape, and the like.

The term "interferon" as used herein refers to a full-length interferon, or an interferon fragment (truncated interferon) or interferon mutant substantially retaining the biological activities of a full-length wild-type interferon (e.g., retaining at least 80%, preferably at least 90%, more preferably at least 95%, 98% or 99% of those of a full length interferon). Interferons include type I interferons (e.g., interferon α and interferon β) and type II interferons (e.g., interferon γ).

The antibody of the present invention or a variant thereof can be applied to prepare various targeted antitumor drugs as well as drugs for diagnosing tumors, in particular, for preparing immune effector cells targeting CD19.

Anti-CD19 Humanized Antibody

The parent antibody of the humanized antibody of the present invention is HD37, which is a mouse IgG1 (Leukocyte Typing II, pp 391-402).

Considering that each of these heavy and light chain variable region sequences can bind to human CD19, the heavy and light chain variable region sequences can be "mixed and matched" to produce the anti-human CD19 binding molecules of the present invention. For example, the light chain variable region of the humanized antibody that binds human CD19 of the present invention is shown in SEQ ID NO: 1 or 7, and the heavy chain variable region is shown in SEQ ID NO: 3 or 5. In a specific embodiment, the humanized antibody binding to human CD19 of the present invention may be: an antibody, comprising a light chain variable region of SEQ ID NO: 1 and a heavy chain variable region of SEQ ID NO: 3; or an antibody comprising a light chain variable region of SEQ ID NO: 1 and a heavy chain variable region of SEQ ID NO: 5; or an antibody comprising a light chain variable region of SEQ ID NO: 7 and a heavy chain variable region of SEQ ID NO: 3; or an antibody comprising a light chain variable region of SEQ ID NO: 7 and a heavy chain variable region of SEQ ID NO: 5.

In another aspect, a variant of an antibody or fragment thereof binding to human CD19 is provided in the present invention. Therefore, an antibody or a fragment thereof is provided in the present invention, which comprises a heavy chain and/or light chain variable region that is at least 80% identical to the heavy or light chain variable region sequence. Preferably, the amino acid sequence identity of the heavy and/or light chain variable regions is at least 85%, more preferably at least 90%, most preferably at least 95%, especially 96%, more particularly 97%, even more particularly 98%, most particularly 99%, including, for example, 80%, 81%, 82%, 83%, 84%, 85%, 86%, 87%, 88%, 89%, 90%, 91%, 92%, 93%, 94%, 95%, 96%, 97%, 98% and 99% of amino acid sequence identity. The identity of the amino acid sequence or the percentage of amino acid residues in sequence that are identical to the humanized antibody or fragment thereof binding to human CD19. Therefore, the sequence identity can be determined by standard methods commonly used to compare the similarity of amino acid positions of two polypeptides. The best match of the respective amino acids of two polypeptides (either along the entire length of one or both sequences or as a predetermined portion along one or both sequences) is aligned using a computer program such as BLAST or FASTA. The program provides default open penalty and default gap penalties, and scoring matrix such as PAM250 (standard scoring matrix; see Dayhoff et al, in Atlas of Protein Sequence and Structure, Volume 5, Supplement 3 (1978)) can be used in combination with computer programs. For example, the percent identity can be calculated as: the total number of identical matches multiplied by 100, divided by the total length of the longer sequences in the matching span and the number of vacancies poured into the longer sequence to align the two sequences.

a humanized antibody fragment that binds to human CD19 is also provided in the present invention, and the fragment is selected from the group consisting of Fab, Fab', Fab'-SH, Fd, dAb, F(ab')2, scFv, bispecific single chain Fv II Poly, diabodies, tribodies and scFvs genetically fused to the same or different antibodies. Preferred fragments are scFv, bispecific single chain Fv dimers and diabody. Full length humanized antibodies that bind to human CD19 is also provided in the present invention.

Characteristics of Humanized Antibody Against Human CD19

Standard assays for assessing the binding ability of an antibody, such as a humanized antibody to human CD19, are known in the art and include, for example, ELISA, Western blot and flow cytometry analysis. Suitable assays are described in detail in the examples. To assess binding, K562 cells stably transfected with CD19 can be used and flow cytometry can be used for determining EC50. In a specific embodiment, binding relative affinity (EC50) of the humanized antibody of the present invention to K562 cells stably transfected with human CD19 is less than 100 nM, preferably less than 10 nM, more preferably between 1 and 10 nM.

Nucleic Acids, Vectors and Host Cells

An isolated nucleic acid encoding a humanized antibody binding to human CD19 and fragments thereof, a vector and a host cell comprising the nucleic acid or vector, are also provided in the present invention. The nucleic acid can be present in an intact cell, cell lysate, or can be in a partially purified or substantially purified form.

The nucleic acid of the invention can be obtained using standard molecular biology techniques, for example, standard PCR amplification or cDNA cloning techniques, thereby obtaining cDNA encoding the light and heavy chains of an antibody or encoding VH and VL segments. For antibodies obtained from immunoglobulin gene libraries (e.g., using phage display technology), one or more nucleic acids encoding the antibodies can be recovered from the library. Methods for introducing foreign nucleic acids into host cells are generally known in the art and can vary with the used host cell.

Preferred nucleic acid molecules of the invention are those encoding a light chain variable region selected from the group consisting of SEQ ID NO: 2, 8, and/or a heavy chain variable region selected from the group consisting of SEQ ID NOs: 4, 6. For expressing a protein, a nucleic acid encoding an antibody of the invention can be integrated into an expression vector. A variety of expression vectors are available for protein expression. Expression vectors can include self-replicating extra-chromosomal vectors, or vectors integrated into the host genome. Expression vectors used in the present invention include, but are not limited to, those which enable expression of proteins in mammalian cells, bacteria, insect cells, yeast, and in vitro systems. As is known in the art, a variety of expression vectors which are commercially available or otherwise available, can be used in the present invention to express antibodies.

Chimeric Antigen Receptor T Cell Containing Anti-CD19 Antibody

In one aspect, a plurality of chimeric antigen receptors (CARs) are provided in the present invention, comprising an antibody or antibody fragment engineered to enhance binding to a CD19 protein. In one aspect, a cell (eg, a T cell) engineered to express CAR is provided in the present invention, wherein the CAR T cell ("CART") exhibits anti-tumor properties. In one aspect, cells are transformed with CAR and CAR is expressed on the cell surface. In some embodiments, cells (e.g., T cells) are transduced with a viral vector encoding CAR. In some embodiments, the viral vector is a lentiviral vector. In some embodiments, the cells can stably express CAR.

In one aspect, the anti-CD19 protein binding portion of a CAR is a scFv antibody fragment. In one aspect, the antibody fragment is functional, whereby it retains an equivalent binding affinity, e.g., it binds to the same antigen with comparable efficacy, as compared with the IgG antibody from which it is derived. In one aspect, the antibody fragment is functional, thereby providing a biochemical reaction, which can include, but is not limited to, activating an immune response, inhibiting the initiation of signaling from its target antigen, inhibiting kinase activity, and the like. In one aspect, the anti-CD19 antigen binding domain of CAR is a scFv antibody fragment that is humanized relative to the murine sequence scFv from which it is derived.

In one aspect, the CAR of the invention combines an antigen binding domain of a specific antibody with an intracellular signaling molecule. For example, in some aspects, intracellular signaling molecules include, but are not limited to, CD3 ξ chain, 4-1BB and CD28 signaling modules, and combinations thereof. In one aspect, a cell (e.g., a T cell) engineered to express a chimeric antigen receptor (CAR) is provided in the present invention, wherein the CAR T cell ("CART") exhibits anti-tumor properties. In one aspect, the antigen binding domain of CAR comprises a humanized anti-CD19 antibody fragment comprising scFV. Accordingly, a CD19-CAR which is engineered and introduced into a T cell and comprises a humanized anti-CD19 binding domain, and a method for using it in adoptive immunotherapy are provided in the present invention.

In one aspect, CD19-CAR comprises at least one intracellular signaling domain, which is selected from the group consisting of a CD137 (4-1BB) signaling domain, a CD28 signaling domain, a CD3 ξ signal domain, and any combination thereof. In one aspect, CD19-CAR comprises at least one intracellular signaling domain derived from one or more co-stimulatory molecules that are not CD137 (4-1BB) or CD28.

In one aspect, in the CAR of the invention, an antigen binding domain of a specific antibody is combined with an intracellular signaling molecule, and an IFNβ expression element is simultaneously. For example, in some aspects, intracellular signaling molecules include, but are not limited to, CD3 ξ chain, 4-1BB and CD28 signaling modules, and combinations thereof. In one aspect, a cell (e.g., a T cell) engineered to express a chimeric antigen receptor (CAR) is provided in the present invention, wherein the CAR T cell ("CART") exhibits anti-tumor properties. In one aspect, the antigen binding domain of CAR comprises a humanized anti-CD19 antibody fragment comprising scFV. On the other hand, an IFNβ expression element is reversely added at the end of the CAR termination signal, including 6 repeated NFAT-AP-1 transcriptional regulatory binding fragment NFATs, IL-2 mini promoter, IFNb cDNA sequence and termination signal PA2. Therefore, CD19-CAR and IFNβ which are engineered and introduced into T cells and comprise a humanized anti-CD19 binding domain, and methods for using them in adoptive immunotherapy are provided in the present invention.

Advantages of the Invention

1. Compared with a murine antibody, no anti-antibody reaction (AAR) and human anti-mouse antibody reaction (HAMA) will be produced by the antibody of the present invention;

2. The antibody of the present invention will not be rapidly cleared by neutralization from an anti-antibody, and exhibit an immunological effector function such as ADCC and CDC;

3. Compared with a murine antibody, the affinity of the antibody of the present invention is not reduced, but also slightly better than the murine antibody; and 4. The antibody of the present invention exhibits advantages, such as high degree of aggregation, good yield, and is easy to be produced and purified.

The invention is further illustrated below in conjunction with specific embodiments. It is to be understood that the examples are not intended to limit the scope of the invention. The experimental methods in the following examples which do not specify specific conditions are usually performed according to conventional conditions such as those described in J. Sambrook et al., Molecular Cloning Experiment Guide, Third Edition, Science Press, 2002, or according to the conditions recommended by the manufacturer.

Example 1. Preparation of Humanized Antibody huHD37 of Antibody HD37 Against CD19

In the present example, murine antibody HD37 (J Immunol. 1987 May 1; 138(9): 2793-9) was used as a parent antibody, and murine antibody HD37 has the light chain variable region as shown in SEQ ID NO: 19 and heavy chain variable region as shown in SEQ ID NO: 20. 6 CDR region sequences of the antibody light and heavy chains were determined by combining 3 naming schemes, Kabat, Chothia and IMGT for antibody CDR regions:

the light chain variable region (SEQ ID NO: 19), wherein the CDR regions are underlined.

DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLE the heavy chain variable region (SEQ ID NO: 20), wherein the CDR regions are underlined

QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSS a. Selection of Antibody Templates germline sequence IGHV1-69*01 (SEQ ID NO: 43)+ IGHJ6*01 (SEQ ID NO: 44) from IMGT database were selected as an antibody template for HD37 heavy chain, and germline sequence IGKV7-3*01 (SEQ ID NO: 45)+ IGKJ1*01 (SEQ ID NO: 46) from IMGT database were selected as an antibody template for HD37 light chain b. CDR Transplantation The light chain CDR regions of HD37 antibody was used to replace the CDR regions of the antibody template IGKV7-3*01+IGKJ1*01 to constitute the light chain variable region of the humanized antibody huHD37 (amino acid sequence is shown in SEQ ID NO: 1). The heavy chain CDR regions of HD37 antibody was used to replace the CDR regions of the antibody template IGHV1-69*01+IGHJ6*01, and the $27^{th}$ glycine in IGHV1-69*01 (SEQ ID NO: 43) was mutated to tyrosine thereby constituting the heavy chain variable region of the humanized antibody huHD37 (amino acid sequence is shown in SEQ ID NO: 3).

Figure 1:
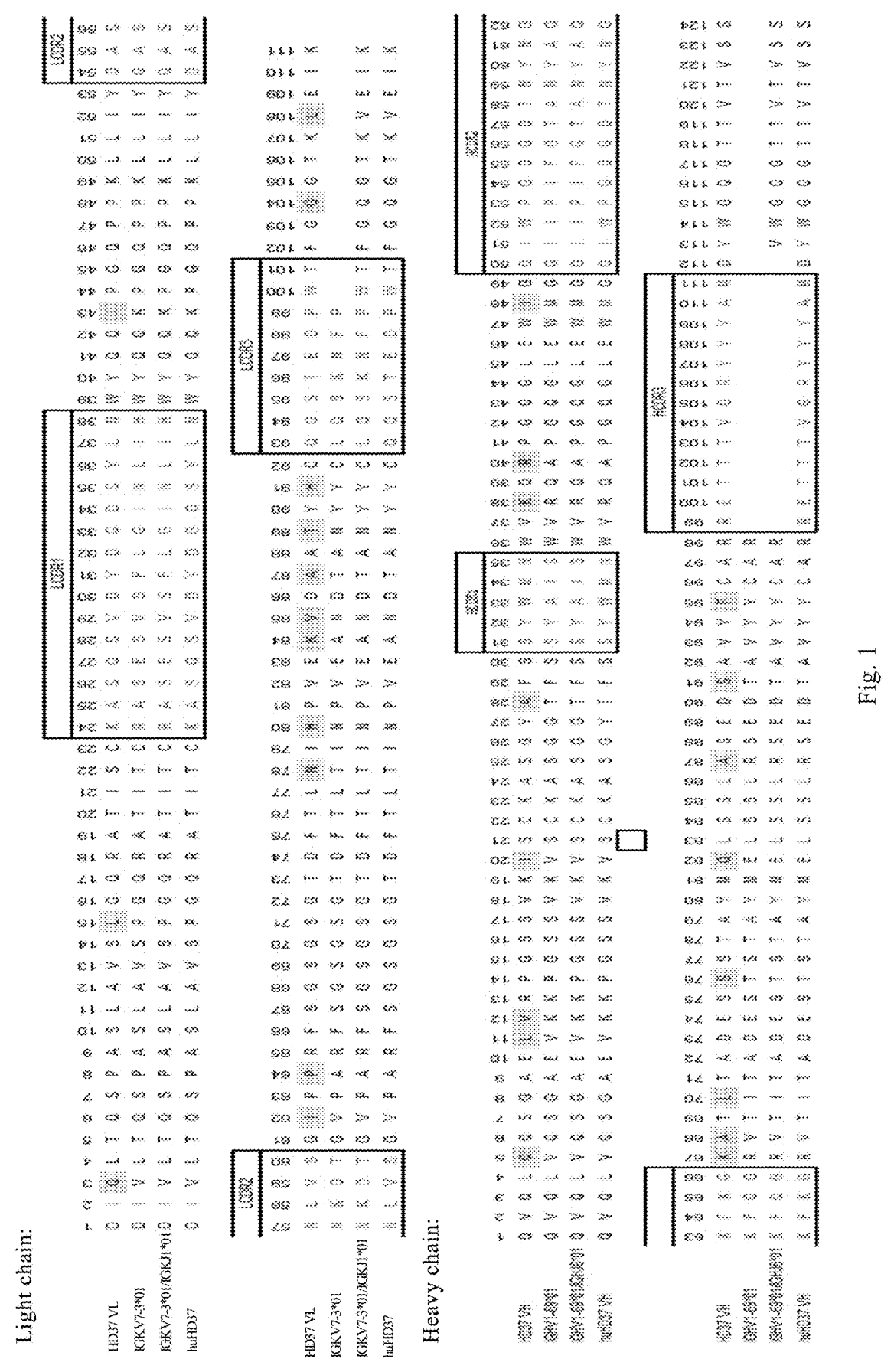

Sequence alignment of huHD37 light chain variable region with HD37, VK7-3*01, VK7-3*01/J1*01, and sequence alignment of huHD37 heavy chain variable region with HD37, VH1_69*01, VH1_69*01/J1*01 are shown in FIG. 1.

c. Expression and Purification of the Humanized Antibody in a Form of scFv_Fc a light chain variable region nucleotide sequence (SEQ ID NO: 2) and heavy chain variable region nucleotide sequence (SEQ ID NO: 4) were designed and synthesized based on the light chain variable region (SEQ ID NO: 1) and heavy chain variable region (SEQ ID NO: 3) of humanized antibody huHD37.

Primers were designed for the light chain nucleotide sequence (SEQ ID NO: 2) and the heavy chain nucleotide sequence (SEQ ID NO: 4), respectively, and a linker consisting of 15 flexible amino acids GGGGSGGGGSGGGGS (SEQ ID NO: 42) was introduced for constituting a scFv (SEQ ID NO: 21), wherein the $1^{st}$-$124^{th}$ position is a heavy chain variable region, and the $140^{th}$-$251^{th}$ position is a light chain variable region; a suitable restriction site and protective bases were introduced upstream to VH, and a suitable restriction site and protective bases were introduced downstream to VL. The PCR product was analyzed by 1% agarose gel electrophoresis, purified and recovered, which, upon digestion, was ligated into eukaryotic expression vector V152 containing human Fc fragment (purchased from Shanghai Ruijin Biotechnology Co., Ltd.).

d. Transient Transfection into 293F Cells by 293Fectin and Expression

1) One day before transfection, 6-7×10$^5$/ml 293F cells were inoculated in a 125 ml culture flask; and on the day of transfection, 3×10$^7$ cells were adjusted into 28 ml FreeStyle™ 293 expression medium;

2) 30 ug DNA was diluted with Opti-MEM I in a final volume of 1 ml, and mixed well; 60 ul 293Fectin™ was diluted with Opti-MEM I in a final volume of 1 ml, and mixed well; After incubated for 5 minutes at room temperature, the diluted DNA was mixed with 293Fectin™; after incubated for 20 minutes at room temperature, 2 ml of DNA-293fectin complex was added to 28 ml of cells, cultured at 37° C., 8% $CO_2$ and 125 rpm for 5 to 7 days, and the supernatant was collected to obtain a lipid-DNA complex.

3) 293F culture supernatant was collected by centrifugation, filtered through a 0.45 um filter, and subjected to affinity-chromatography through rProtein A column to obtain a humanized antibody huHD37.

4) Antibody aggregation was analyzed by SEC, the results are shown in FIG. 2, wherein the antibody in a monomer form accounted for 94.3%, the proportion of the antibody in a monomer form is significantly higher than that of the conventional humanized antibody, and compared with the murine antibody HD37, the aggregation degree is also significantly reduced.

Figure 3:
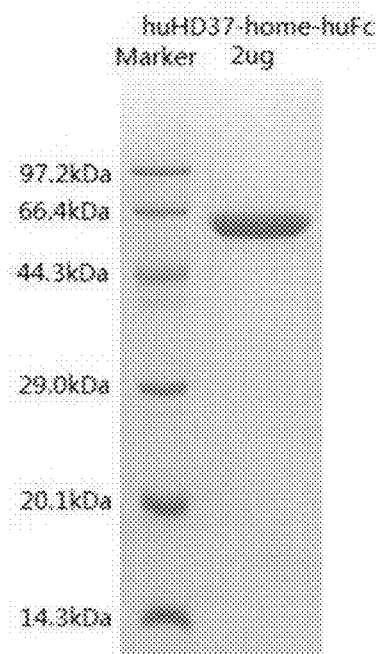
FIG. 3 shows SDS PAGE gel electrophoresis of purified huHD37 under reducing conditions.

5) After concentration by ultrafiltration, the obtained antibodies were quantitatively and qualitatively analyzed by SDS PAGE. As shown in FIG. 3, under the reducing condition, a single band at 50 Kd size is the target protein, and the yield is 66 ug/ml (yield=weight of final product/transfection volume), which is much higher than that of the antibody in CN102209556A, which is 5-25 mg/L.

e. Binding Properties of Humanized Antibody huHD37

Figure 4:
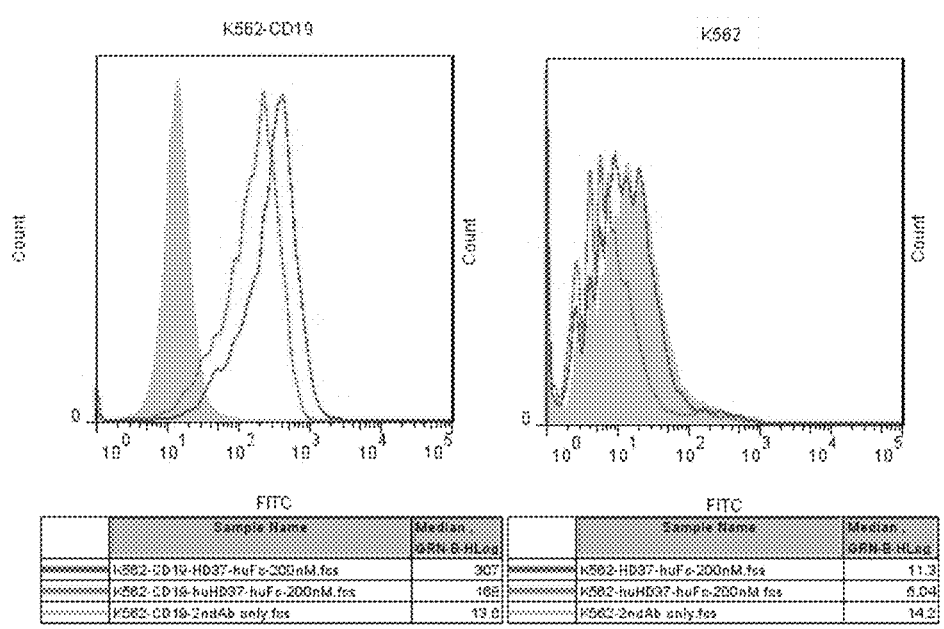
FIG. 4 shows the binding of purified HD37, humanized antibody huHD37 to K562-CD19 and K562 cells as determined by flow cytometry.
Figure 5:
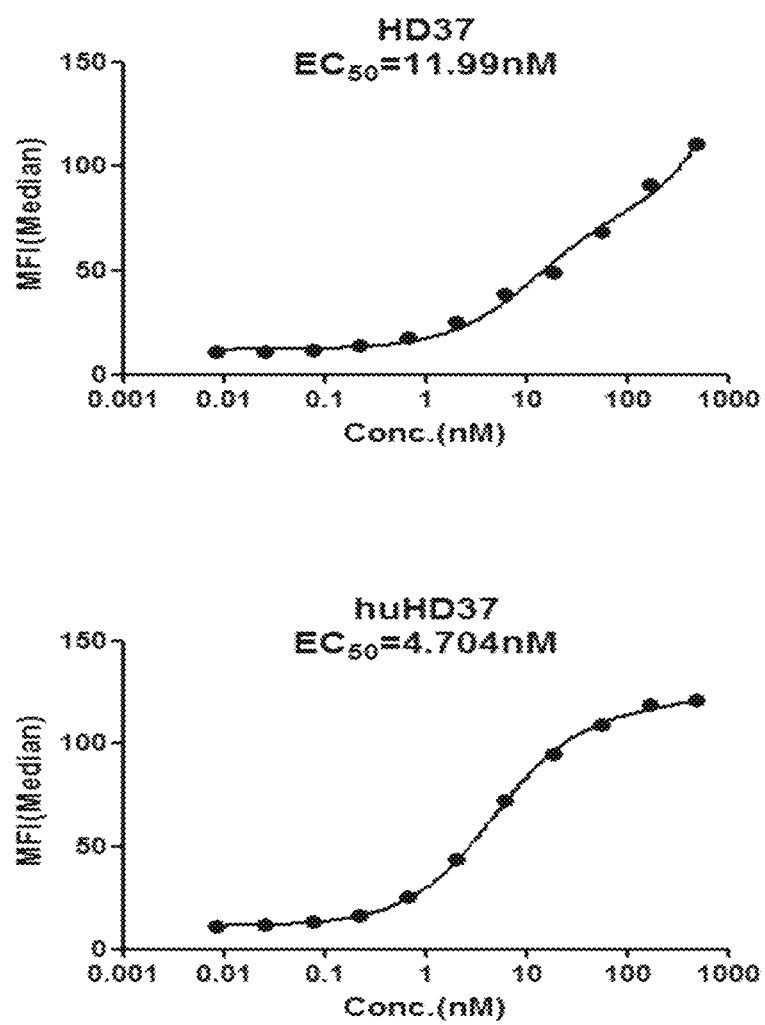
FIG. 5 shows the relative binding affinity of HD37 and the humanized antibody huHD37, in which scFv is conjugated to human IgG1 Fc, to K562 cells stably transfected with human CD19.

K562 cells (K562-CD19) stably expressing human CD19 and K562 were used, and cells were harvested, washed with complete growth medium and plated into U-bottom microtiter plates at approximately 1-5×10$^5$ cells/well. The gradient-diluted huHD37 scFv_Fc fusion antibody was incubated with K562-CD19/K562 for 30 minutes on ice, and then incubated with FITC-labeled anti-human Fc as a secondary antibody. After two washing steps, the analysis was performed using Guava easyCyte™ HT System, and the experimental data was processed using GraphPad Prism to obtain an EC50. FIG. 4 shows the binding of HD37 and huHD37 to K562-CD19 and K562 cells. The results indicated that humanized huHD37 and the parental antibody HD37 specifically bind to K562 cells stably transfected with CD19 while not binding to K562 cells. FIG. 5 shows the relative binding affinities (EC50) of HD37 and humanized huHD37 scFv, after being chimeric with human IgG1 Fc portion, to HEK293 cells stably transfected with human CD19. Compared with the parental HD37, the affinity of the humanized antibody huHD37 was improved.

Example 2. Modification of huHD37

In the present example, huHD37 was used as a a parent antibody, and huHD37 was modified by phage display method. In the construction of a phage library based on the humanized antibody huHD37, the CDR3 regions of the light chain and heavy chain were retained, and two phage libraries were constructed by using degenerate primers and randomizing CDR1 and CDR2 of the light chain or CDR1 and CDR2 of the heavy chain, respectively. Primer information is shown in the table below.

| SEQ ID NO: | Name | Sequence | Length |
|---|---|---|---|
| 43 | LMF | caggaaacag ctatgaccat gattac | 26 |
| 44 | C37H1R | cactccaggc cctggccggg ggcctgccgc acccamnnmn nmnnmnnmnn mnngaaggtgtagccgctgg cct | 73 |
| 45 | C37H2F | ccggccaggg cctg-gagtgg atgggcnnka tcnnkcccnn knnkggcnnk accnnktacaacggcaagtt caagggc | 77 |
| 46 | FdR | gacgttagta aatgaatttt ctgtat-gagg | 30 |
| 47 | C37L1R | ctggccggc ttctgctggt accamnnmnn gtamnnmnnm nnmnnmnnmn nmnngctmnngctggccttg cagg | 74 |

-continued

| SEQ ID NO: | Name | Sequence | Length |
|---|---|---|---|
| 48 | C37L2F | accagcagaa gcccggccag ccccc-caagc tgctgatcta cnnknnkagc nnkctgnnkagcggcgtgcc cgcccggttc | 80 |

2.1 Construction of huHD37 Mutant:

The template plasmid was firstly constructed based on the antibody huHD37 (scFv) (amino acid sequence can be found in SEQ ID NO: 21, and nucleotide sequence can be found in SEQ ID NO: 22). For phage libraries of randomization of light chain CDR1 and CDR2, primers LMF and C37L1R were used in PCR for amplifying fragment 1; primers C37L2F and FdR were used in PCR for amplifying fragment 2; and then fragment 1 and fragment 2 were ligated by bridge PCR to obtain a full length scFv containing a randomized sequence. And then the full-length fragment was digested with NcoI and NotI, ligated into the same digested template plasmid by T4 ligase, and electroporation-transformed into TG1 competent cells with a storage capacity of 1.76E+9. For phage libraries of randomization of heavy chain CDR1 and CDR2, primers LMF and C37H1R were used in PCR for amplifying fragment 3; primers C37H2F and FdR were used in PCR for amplifying fragment 4; and then fragment 3 and fragment 4 were ligated by bridge PCR to obtain a full length scFv containing a randomized sequence. And then the full-length fragment was digested with NcoI and NotI, ligated into the same digested template plasmid by T4 ligase, and electroporation-transformed into TG1 competent cells with a storage capacity of 1.9E+9.

Figure 6:
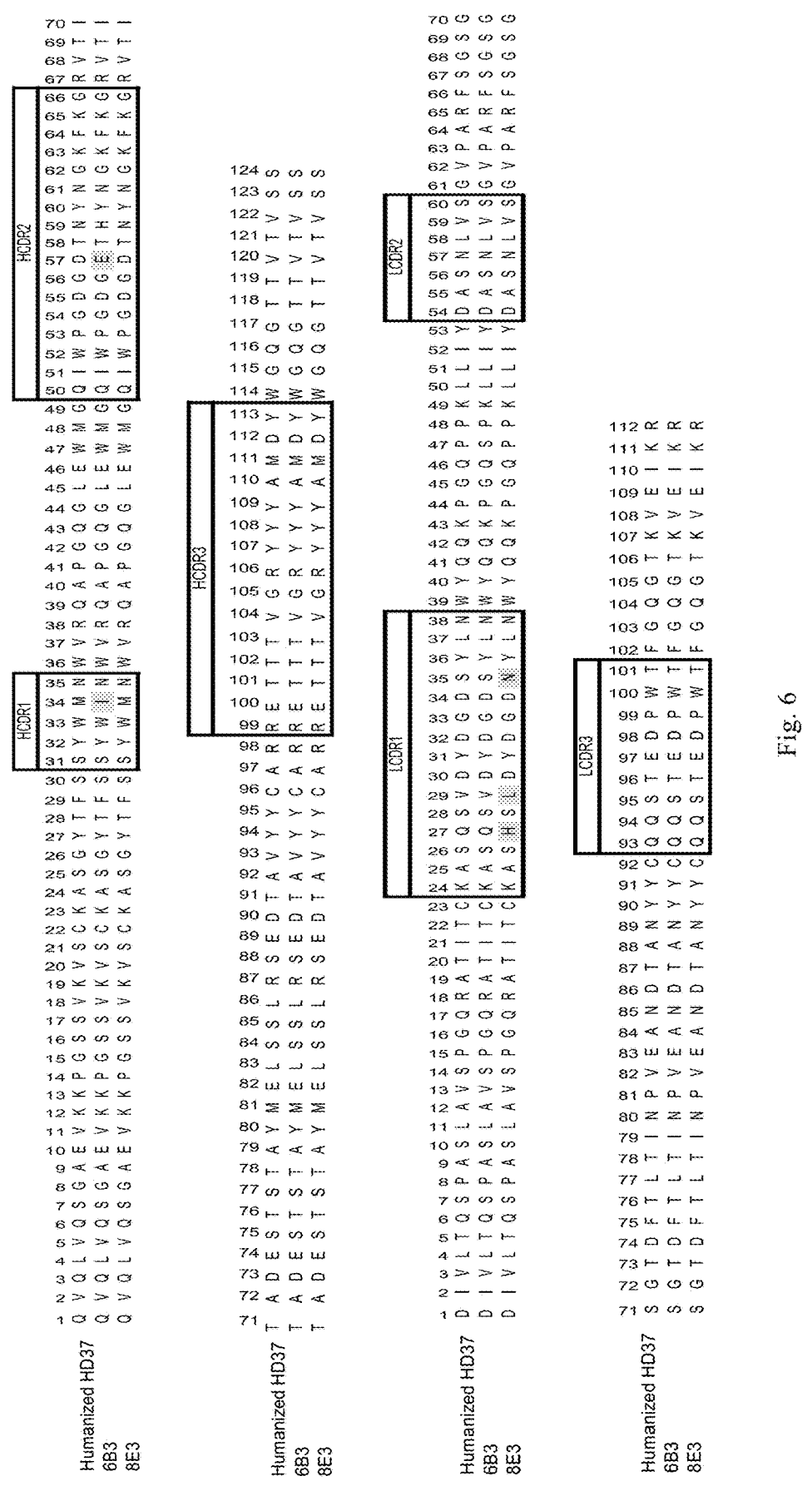

Screening of phage libraries. K562-CD19 cells were collected, washed twice with PBS, and 1E+7 cells were resuspended in 2 ml of 4% MPBS (4 g skim milk powder dissolved in 100 ml PBS), and 1 ml ($10^{13}$ phage) phage library was added to the cells, placed on a rotator, slowly rotated for an hour and a half, and then stand for half an hour. The non-specific phage was subsequently washed off, and the bound phage was eluted and used to infect E. coli TG1 in logarithmic growth phase. The eluted phages were expanded and the expanded phage library was purified employing PEG/NaCl precipitation for the next round of screening. Panning was performed for 2 cycles to enrich scFv phage clones specifically binding to K562-CD19. Positive clones were determined by flow cytometry as shown in Example 1. Multiple clones were obtained which were consistent with the parental antibody huHD37. FIG. 6 compares amino acid sequences of 6B3, 8E5 and the humanized antibody huHD37, wherein, compared with the parent antibody huHD37, there are two point mutations on the heavy chain of clone 6B3 (SEQ ID NO: 5), one on CDR1, methionine at position 34 to isoleucine, and one on CDR2, aspartic acid at position 57 to glutamic acid. Compared to the parental antibody huHD37, there are 3 point mutations on the light chain of Clone 8E3 (SEQ ID NO: 7), which are located in CDR1 region, glutamine at position 27 to histidine, valine at position 29 to leucine and serine at position to asparagine.

2.2 Expression and Purification of Clone 6B3, 8E3 (scFv_Fc)

Figure 7:
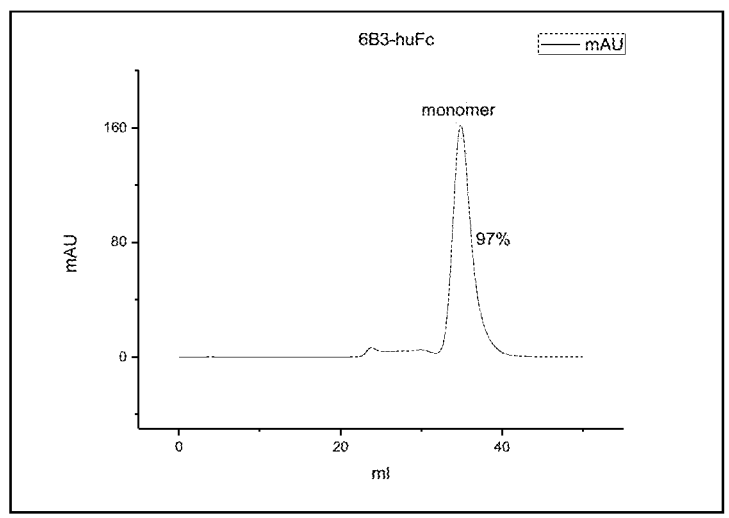
FIG. 7 shows SEC analysis on the aggregation of clone 6B3 (scFv_Fc)
Figure 8:
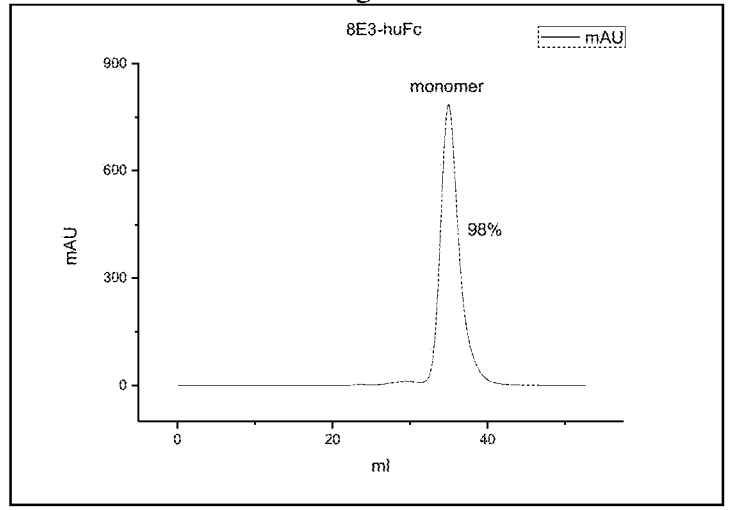
FIG. 8 shows SEC analysis on the aggregation of clone 8E3 (scFv_Fc)

As shown in Example 1, a suitable cleavage site and a protective base were introduced upstream to VH, and a suitable cleavage site and a protective base were introduced downstream to VL. The PCR product was analyzed on 1% agarose gel, purified and recovered. After digestion, it was ligated into eukaryotic expression vector V152 containing human Fc fragment (purchased from Shanghai Ruijin Biotechnology Co., Ltd.), transiently transfected into 293F cells by 293Fectin, expressed, and subjected to affinity-chromatography through rProtein A column to obtain humanized antibody huHD37. The aggregation of the antibody was analyzed by SEC, and as shown in FIGS. 7 and 8, the antibody in the monomer form accounted for 97% and 98%, respectively, which, compared with the parental antibody huHD37, increased by 3% and 4%, respectively, and the degree of aggregation was further reduced. After concentration by ultrafiltration, the obtained antibodies were quantitatively and qualitatively analyzed by SDS PAGE. The yields were 12.8 ug/ml and 69 ug/ml, respectively (yield=weight of final product/transfection volume).

2.3 Binding Characteristics of 6B3, 8E3

Figure 9:
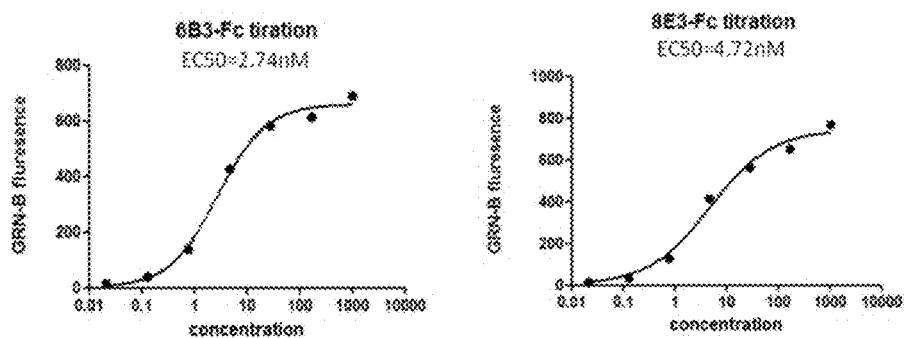
FIG. 9 shows the relative binding affinity of 6B3,8E3 (scFv_Fc) to K562 cells stably transfected with human CD19.

K562 cells stably expressing human CD19 (K562-CD19) and K562 were used, and cells were harvested, washed with complete growth medium, and plated into U-bottom microtiter plates at approximately $1-5 \times 10^5$ cells/well. The gradient diluted scFv_Fc fusion antibody was incubated with K562-CD19/K562 for 30 minutes on ice, and then incubated with FITC-labeled anti-human Fc as a secondary antibody. After two washing steps, the analysis was performed using Guava easyCyte™ HT System, and the experimental data was processed using GraphPad Prism to obtain an EC50. FIG. 9 shows the binding of 6B3 and 8E3 to K562-CD19 and K562 cells. The results showed that the two clones 6A3, 8E3 with increased stability and reduced aggregation exhibited substantially consistent, even improved binding abilities to K562-CD19, as compared with huHD37.

Example 3. Construction of Anti-CD19 Chimeric Antigen Receptor Plasmid (CAR)

3.1 Construction of Humanized Antibody Chimeric Antigen Receptor Plasmid (CAR)

Figure 10:
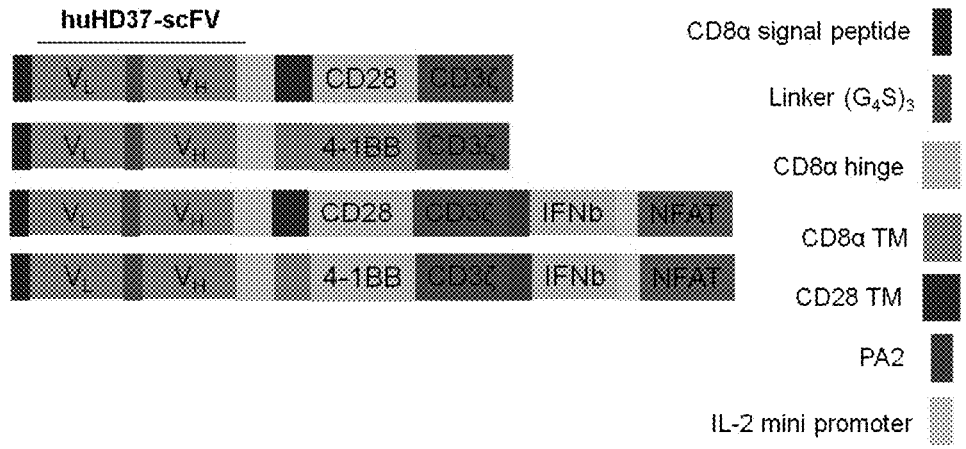
FIG. 10 shows a schematic diagram of the structure of huHD37 CAR.

Lentiviral plasmids expressing the second and fourth generation of chimeric antigen receptors of humanized antibody huHD37 were constructed using PRRLSIN-cPPT.EF-1α as a vector, including PRRLSIN-cPPT.EF-1α-huHD37-28Z, PRRLSIN-cPPT.EF-1α-huHD37-BBZ, PRRLSIN-cPPT.EF-1α-huHD37-28Z&IFNb and PRRLSIN-cPPT.EF-1α-huHD37-BBZ&IFNb (FIG. 10). The huHD37-28Z sequence consists of CD8α signal peptide (SEQ ID NO: 23), huHD37 scFV, CD8 hinge (SEQ ID NO: 25), CD28 transmembrane domain (SEQ ID NO: 27), intracellular signaling domain (SEQ ID NO: 29) and intracellular domain CD3ξ of CD3 (SEQ ID NO: 31); the huHD37-BBZ sequence consists of CD8α signal peptide (SEQ ID NO: 23), huHD37scFV, CD8 hinge (SEQ ID NO: 25), transmembrane domain (SEQ ID NO: 33), CD137 intracellular signaling domain (SEQ ID NO: 35) and CD34 (SEQ ID NO: 31); huHD37-28BBZ sequence consists of CD8α signal peptide (SEQ ID NO: 23), huHD37-scFV, CD8 hinge (SEQ ID NO: 25), CD28 transmembrane domain (SEQ ID NO: 27) and intracellular domain (SEQ ID NO: 29), CD137 intracellular signaling domain (SEQ ID NO: 35) and CD3ξ (SEQ ID NO: 31). In PRRLSIN-cPPT.EF-1α-huHD37-28Z&IFNb and PRRLSIN-cPPT.EF-1α-huHD37-BBZ&IFNb, 6 repeats of NFAT-AP-1 transcriptional regulatory binding fragment NFAT (SEQ ID NO: 37), IL-2 mini promoter (SEQ ID NO: 38), IFNb cDNA sequence (SEQ ID NO: 39) and termination signal PA2 (SEQ ID NO: 41) were reversely added at the end of huHD37-28Z and huHD37-BBZ CAR termination signals.

3.2 Preparation of Lentiviral Transduced T Lymphocyte-CAR-Positive T Lymphocyte

1) T lymphocyte activation: T lymphocytes were cultured in a lymphocyte culture medium at a density of about $1\times10^6$/mL, magnetic beads (Invitrogen) simultaneously coated with anti-CD3 and CD28 antibodies were added at a magnetic bead:cell ratio of 2:1, and incubated with recombinant human IL-2 (Shanghai Huaxin Biotech Co., Ltd.) at a final concentration of 500 U/mL for 48 h;

2) Retronectin coated 24-well plates: 380 μl of 5 pg/ml retronectin solution (PBS) per well was added and incubated overnight at 4 degrees;

3) The retronectin solution (PBS) in a 24-well plate was discarded and the plate was washed twice with 1 ml PBS;

4) The cells were inoculated in a 24-well plate coated with retronectin, the number of cells per well was $3\times10^5$, and the volume of the culture solution was 600 μl;

5) Concentrated lentivirus was added to PBMC cells according to MOI=10, centrifuged for 40 min at 32° C., 1800 rpm and transferred to a cell culture incubator;

6) Amplification culture: infected cells were passaged every other day at a density of $5\times10^5$/mL, and recombinant human IL-2 at a final concentration of 500 U/mL was added to the lymphocyte culture solution.

3.3 Expression of T Lymphocyte Chimeric Antigen Receptor

1) On day 7, $1\times10^6$ Lentivirus-infected T lymphocytes were taken and aliquoted into 2 ml centrifuge tubes;

2) T lymphocytes were centrifuged at 4 degrees, 5000 rpm for 5 min, the supernatant was discarded, and T lymphocytes were washed twice with PBS;

3) In the control group, 50 μl of PE-SA (1:200 dilution) antibody was added to cells and incubated for 45 min on ice, washed twice with PBS (2% NBS), and resuspended as a control;

4) In test group, cells+50 μl 1:50 diluted biotin-Goat anti human IgG, F(ab')2 antibody were incubated on ice for 45 min; and washed twice with PBS (2% NBS); 50 μl PE-SA (1:200 dilution) antibody was added and incubated on ice for 45 min;

5) Cells were resuspended in 2 ml PBS (2% NBS), centrifuged at 4 degrees, 5000 rpm/min for 5 min to discard the supernatant, repeated twice;

6) 500 μl PBS (2% NBS) was added and transferred to a flow tube. PE channel was detected by flow cytometry to determine the proportion of CAR-positive T cells.

Figure 11:
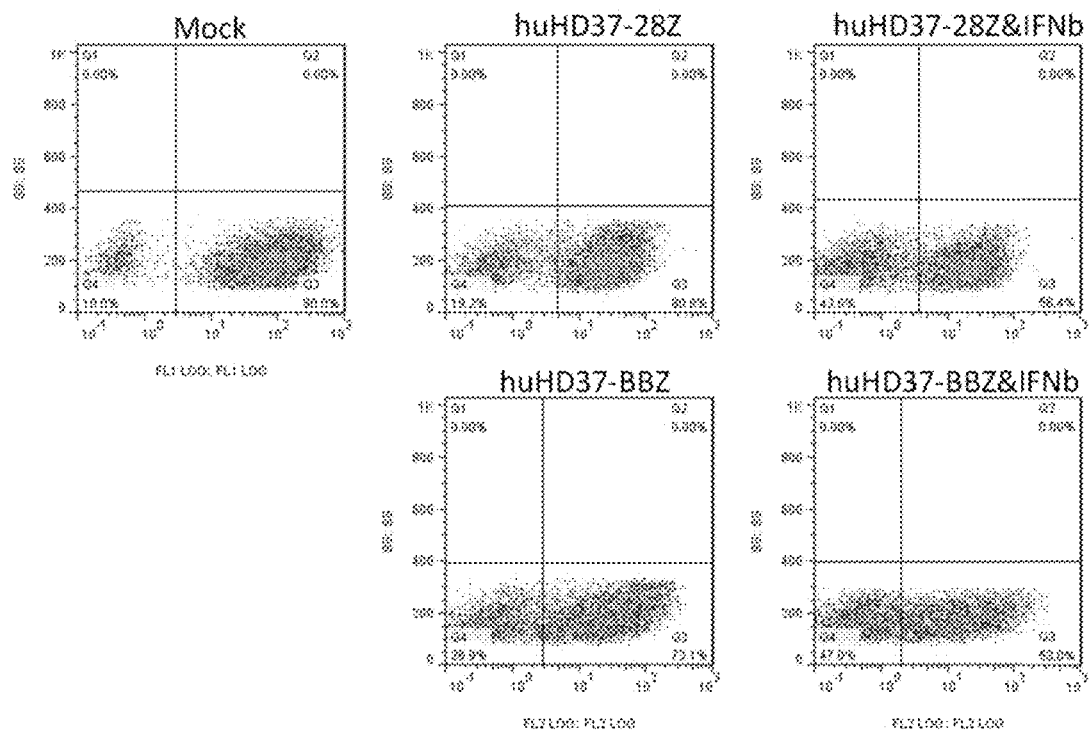
FIG. 11 shows the positive rates of huHD37 CAR+ T and Mock+ T cells.

7) Flow detection results: positive rate of CAR+ T cells after lentiviral infection was (FIG. 11):

huHD37-28Z+T cell positive rate: 80.8%
huHD37-BBZ+T cell positive rate: 73.1%
huHD37-28Z & IFNb+T cell positive rate: 56.4%
huHD37-BBZ & IFNb+T cell positive rate: 53%

In addition, the positive rate of Mock+T cells in the control group was 90%.

3.4 Analysis of the Exposure of CD19 Antigen Epitope on Tumor Cell Lines

Figure 12:
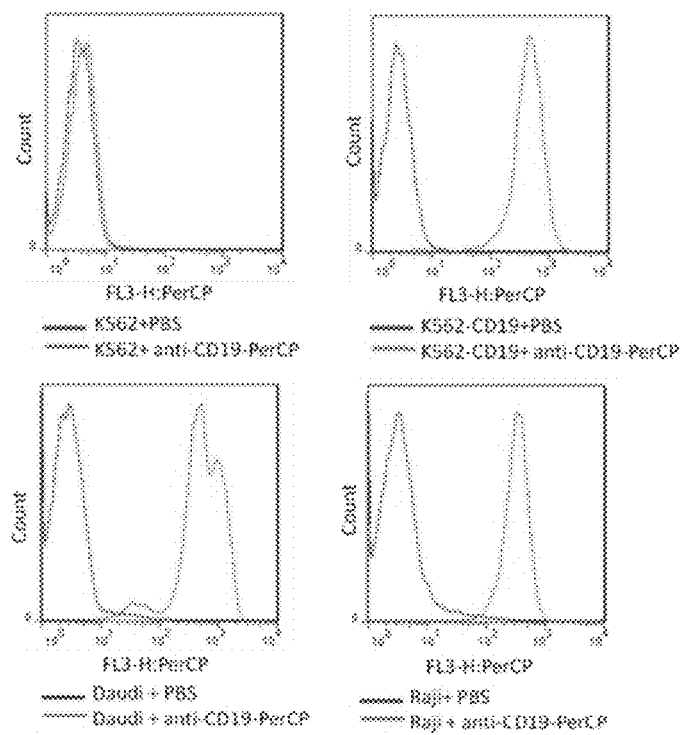
FIG. 12 shows the exposure of CD19 epitope on tumor cell lines.

1) Following tumor cells were incubated in 10 cm plates: K562, K562-CD19, Daudi and Raji cells;

2) $1\times10^6$ of the above cells were taken, aliquoted, and centrifuged at 4° C., 5000 rpm/min for 5 minutes;

3) A group of cells were directly resuspended in 500 μl PBS (1% NBS) as a control;

4) A group+50 μl 1:20 diluted PerCP-CD19 antibody were incubated on ice for 45 min;

5) Cells were resuspended in 2 ml of PBS (1% NBS), centrifuged at 4° C., 5000 rpm/min for 5 minutes to discard the supernatant, and repeated twice;

6) Cells were resuspended in 500 μl PBS (1% NBS) and transferred to a flow tube;

7) PerCP channel was detected by Flow cytometry;

8) Flow cytometry results showed that K562 cells did not express CD19 protein, and K562-CD19, Daudi and Raji were CD19-positive cells (FIG. 12).

3.5 Determination of Cytotoxicity of Targeting CAR T Cells of huHD37

1) Target cells: 75 pL of $2\times10^5$/mL K562, K562-CD19, Daudi and Raji cells were inoculated in 96 well plates respectively;

2) Effector cells: T-Mock and CAR T cells expressing different chimeric antigen receptors were added at a effector and target ratio of 3:1, 1:1 or 1:3;

3) Quadraplicate wells were set in each group, and the average value of quadraplicate wells was taken. The detection time was 18 h;

4) Each experimental group and each control group are as follows:

Each experimental group: each target cell+CAR T expressing different chimeric antigen receptors;

① spontaneous LDH release from effector cells: correcting LDH spontaneously released from effector cells;

② spontaneous LDH release from target cells: correcting LDH spontaneously released from target cells;

③ maximum LDH release from target cells: determining 100% LDH release based on the control;

④ Volume Correction Control: correcting change in the volume due to the addition of lysate (10×);

⑤ Medium Background Control: correcting LDH activity produced by serum in the medium and background absorption by phenol red.

5) Detection method: CytoTox 96 non-radioactive cytotoxicity test kit (Promega) was used. Specific instructions can be found in CytoTox 96 Non-Radioactive Cytotoxicity Assay Kit.

6) The cytotoxicity calculation formula is: % cytotoxicity=[(experimental group−effector cell spontaneous group−target cell spontaneous group)/(target cell maximum−target cell spontaneous)]*100.

Before the calculation, the medium control shall be subtracted from the effector cell control, the target cell control and the experimental group; and the volume control shall be subtracted from the target cell maximum lysis amount.

Figure 13:
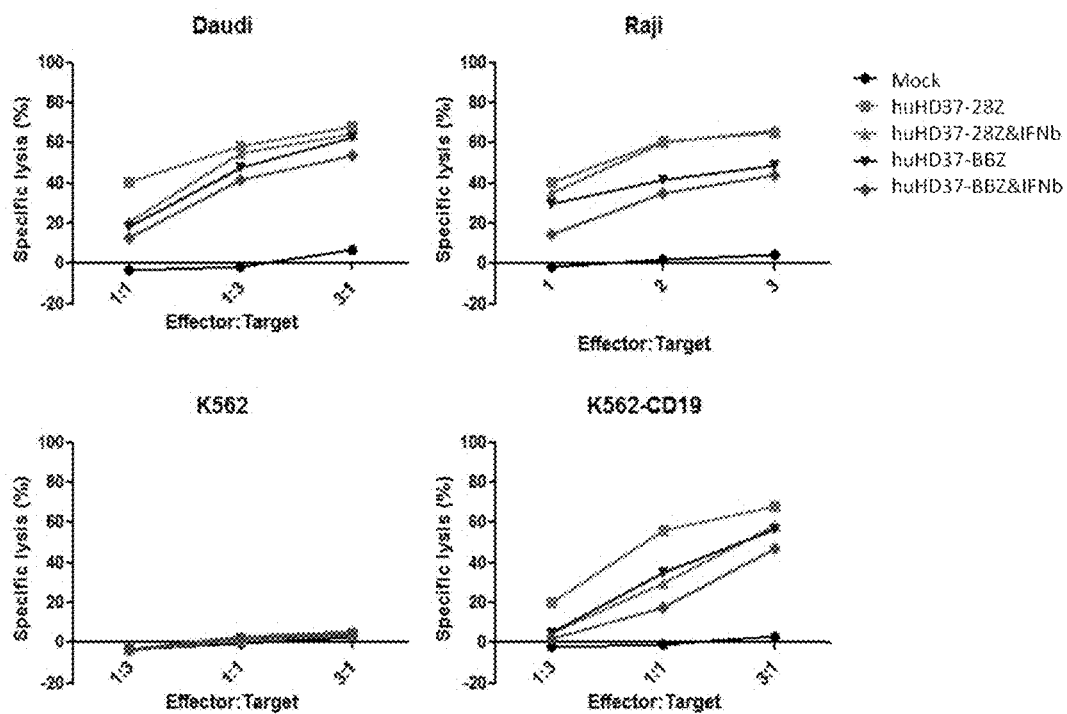
FIG. 13 compares in vitro activities of the second and fourth generation of huHD37 CART cells.

7) The results showed that each of the CAR T cells expressing different chimeric antigen receptors exhibited significant in vitro killing activity against CD19-positive cells, and no significant non-specific killing against CD19-negative K562 cells (FIG. 13).

Example 4. Construction of Anti-CD19 Chimeric Antigen Receptor Plasmid (CAR)

Applicant repeated Example 3 by using clones 6B3, 8E3 obtained in Example 2, and results showed that 6B3 and 8E3 produced similar effects as huHD37.

All documents mentioned in the present application are hereby incorporated by reference in their entireties as if each document is separately cited as a reference. In addition, it is to be understood that various modifications and changes may be made by a skilled person in the art, after reading the above teachings of the present invention, and the equivalent forms also fall within the scope defined by the claims appended hereto.

The invention claimed is:

1. An antibody that binds CD19, wherein the antibody comprises a light chain variable region (VL) comprising light chain complementarity determining region (LCDR) 1, 2, and 3 and comprises a heavy chain variable region (VH) comprising heavy chain complementarity determining region (HCDR) 1, 2, and 3; wherein the antibody is selected from the group consisting of:

(a) an antibody having a light chain variable region of SEQ ID NO: 1 and a heavy chain variable region that has HCDR1 as shown in SEQ ID NO: 15, HCDR2 as shown in SEQ ID NO: 16 and HCDR3 as shown in SEQ ID NO: 11;

(b) an antibody having a light chain variable region of SEQ ID NO: 1 and a heavy chain variable region of SEQ ID NO: 5;

(c) an antibody having a light chain variable region of SEQ ID NO: 1 and a heavy chain variable region of SEQ ID NO: 3;

(d) an antibody having a light chain variable region that has LCDR1 as shown in SEQ ID NO: 17, LCDR2 as shown in SEQ ID NO: 13 and LCDR3 as shown in SEQ ID NO: 14 and a heavy chain variable region that has HCDR1 as shown in SEQ ID NO: 15, HCDR2 as shown in SEQ ID NO: 16 and HCDR3 as shown in SEQ ID NO: 11;

(e) an antibody having a light chain variable region that has LCDR1 as shown in SEQ ID NO: 17, LCDR2 as shown in SEQ ID NO: 13 and LCDR3 as shown in SEQ ID NO: 14 and a heavy chain variable region of SEQ ID NO: 5;

(f) an antibody having a light chain variable region that has LCDR1 as shown in SEQ ID NO: 17, LCDR2 as shown in SEQ ID NO: 13 and LCDR3 as shown in SEQ ID NO: 14 and a heavy chain variable region of SEQ ID NO: 3;

(g) an antibody having a light chain variable region of SEQ ID NO: 7 and a heavy chain variable region that has HCDR1 as shown in SEQ ID NO: 15, HCDR2 as shown in SEQ ID NO: 16 and HCDR3 as shown in SEQ ID NO: 11;

(h) an antibody having a light chain variable region of SEQ ID NO: 7 and a heavy chain variable region of SEQ ID NO: 5; and (i) an antibody having a light chain variable region of SEQ ID NO: 7 and a heavy chain variable region of SEQ ID NO: 3.

2. The antibody of claim 1, wherein the antibody comprises an antibody having a light chain variable region of SEQ ID NO: 1 and a heavy chain variable region that has HCDR1 as shown in SEQ ID NO: 15, HCDR2 as shown in SEQ ID NO: 16 and HCDR3 as shown in SEQ ID NO: 11.

3. The antibody of claim 1, wherein the antibody comprises an antibody having a light chain variable region of SEQ ID NO: 1 and a heavy chain variable region of SEQ ID NO: 5.

4. The antibody of claim 1, wherein the antibody comprises an antibody having a light chain variable region of SEQ ID NO: 1 and a heavy chain variable region of SEQ ID NO: 3.

5. The antibody of claim 1, wherein the antibody comprises an antibody having a light chain variable region that has LCDR1 as shown in SEQ ID NO: 17, LCDR2 as shown in SEQ ID NO: 13 and LCDR3 as shown in SEQ ID NO: 14 and a heavy chain variable region that has HCDR1 as shown in SEQ ID NO: 15, HCDR2 as shown in SEQ ID NO: 16 and HCDR3 as shown in SEQ ID NO: 11.

6. The antibody of claim 1, wherein the antibody comprises an antibody having a light chain variable region that has LCDR1 as shown in SEQ ID NO: 17, LCDR2 as shown in SEQ ID NO: 13 and LCDR3 as shown in SEQ ID NO: 14 and a heavy chain variable region of SEQ ID NO: 5.

7. The antibody of claim 1, wherein the antibody comprises an antibody having a light chain variable region that has LCDR1 as shown in SEQ ID NO: 17, LCDR2 as shown in SEQ ID NO: 13 and LCDR3 as shown in SEQ ID NO: 14 and a heavy chain variable region of SEQ ID NO: 3.

8. The antibody of claim 1, wherein the antibody comprises an antibody having a light chain variable region of SEQ ID NO: 7 and a heavy chain variable region that has HCDR1 as shown in SEQ ID NO: 15, HCDR2 as shown in SEQ ID NO: 16 and HCDR3 as shown in SEQ ID NO: 11.

9. The antibody of claim 1, wherein the antibody comprises an antibody having a light chain variable region of SEQ ID NO: 7 and a heavy chain variable region of SEQ ID NO: 5.

10. The antibody of claim 1, wherein the antibody comprises an antibody having a light chain variable region of SEQ ID NO: 7 and a heavy chain variable region of SEQ ID NO: 3.

11. The antibody of claim 1, wherein the antibody is selected from the group consisting of a Fab, Fab', Fab'-SH, Fd, F(ab')2, scFv, bispecific single chain Fv dimer, diabodies, tribodies, and scFvs genetically fused to the same or different antibodies.

12. A CD19 specific chimeric antigen receptor (CAR) comprising an extracellular domain, a hinge domain, a transmembrane domain, and an intracellular signal domain sequentially linked, wherein the extracellular domain comprises an anti-CD19 antibody of claim 1.

13. The chimeric antigen receptor of claim 12, wherein the intracellular signal domain further comprises one or more co-stimulatory signal domains.

14. The chimeric antigen receptor of claim 13, wherein the transmembrane domain is a transmembrane domain of CD8α or CD28; or wherein the co-stimulatory signal domain is the intracellular signal domain of CD137 or CD28.

15. The chimeric antigen receptor of claim 12, wherein the extracellular domain in a single chain antibody comprising a light chain variable region that has LCDR1 as shown in SEQ ID NO: 17, LCDR2 as shown in SEQ ID NO: 13 and LCDR3 as shown in SEQ ID NO: 14 and a heavy chain variable region that has HCDR1 as shown in SEQ ID NO: 15, HCDR2 as shown in SEQ ID NO: 16 and HCDR3 as shown in SEQ ID NO: 11.

16. A genetically modified immune cell which expresses the chimeric antigen receptor of claim 12.

17. The genetically modified immune cell of claim 16, wherein the genetically modified immune cell further expresses a sequence that is a cytokine selected from IL-12, IL-15, IL-21 or type I interferon or a sequence that is a safety switch.

18. A genetically modified T cell which expresses the chimeric antigen receptor of claim 15.

19. A multifunctional immunoconjugate, comprising an antibody of claim 1 and a functional molecule linked thereto, wherein the functional molecule is selected from the group consisting of a molecule that targets tumor surface markers other than CD19, a molecule that inhibits tumors, a molecule that targets a surface marker on an immune cell, or a detectable label; wherein the multifunctional immunoconjugate optionally comprises a linker peptide between the antibody and functional molecule.

20. The multifunctional immunoconjugate of claim 19, wherein the molecule that inhibits tumors is an antitumor cytokine or an antitumor toxin.

21. The multifunctional immunoconjugate of claim 19, wherein the molecule that targets a surface marker of an immune cell is an anti-CD3 antibody.

22. A pharmaceutical composition comprising an antibody of claim 1.

23. A pharmaceutical composition comprising genetically modified T cells of claim 18.

24. A pharmaceutical composition comprising a multifunctional immunoconjugate of claim 19.

25. A CD19 specific chimeric antigen receptor, wherein the chimeric antigen receptor is selected from the group consisting of:

chimeric antigen receptor huHD37-28Z, which has an extracellular domain as shown in SEQ ID NO: 21, a hinge domain as shown in SEQ ID NO: 25, a transmembrane domain as shown in SEQ ID NO: 27, a co-stimulatory signal domain as shown in SEQ ID NO: 29, and a primary signal domain as shown in SEQ ID NO: 31;

chimeric antigen receptor huHD37-BBZ, which has an extracellular domain as shown in SEQ ID NO: 21, a hinge domain as shown in SEQ ID NO: 25, a transmembrane domain as shown in SEQ ID NO: 33, a co-stimulatory signal domain as shown in SEQ ID NO:35, and a primary signal domain as shown in SEQ ID NO: 31; and chimeric antigen receptor huHD37-28BBZ, which has an extracellular domain as shown in SEQ ID NO: 21, a hinge domain as shown in SEQ ID NO: 25, a transmembrane domain as shown in SEQ ID NO: 27, costimulatory signal domains as shown in SEQ ID NO: 29 and SEQ ID NO: 35, and a primary signal domain as shown in SEQ ID NO: 31.

26. A genetically modified T cell which expresses a CD19 specific chimeric antigen receptor of claim 25.

27. A pharmaceutical composition comprising genetically modified T cells of claim 26.

28. A method of killing a CD19-expressing tumor cell comprising contacting the tumor cell with genetically modified T cells of claim 26.

* * * * *

SEQUENCE LISTING

<160> NUMBER OF SEQ ID NOS: 56

<210> SEQ ID NO 1
<211> LENGTH: 112
<212> TYPE: PRT
<213> ORGANISM: Artificial sequence
<220> FEATURE:
<223> OTHER INFORMATION: huHD37 VL amino acid sequence

<400> SEQUENCE: 1

Asp Ile Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Thr
                85                  90                  95

Glu Asp Pro Trp Thr Phe Gly Gln Gly Thr Lys Val Glu Ile Lys Arg
            100                 105                 110

<210> SEQ ID NO 2
<211> LENGTH: 336
<212> TYPE: DNA
<213> ORGANISM: Artificial sequence
<220> FEATURE:
<223> OTHER INFORMATION: huHD37 VL nucleotide sequence

<400> SEQUENCE: 2
gacatcgtgc tgacccagag ccccgccagc ctggccgtga gccccggcca gcgggccacc        60
atcacctgca aggccagcca gagcgtggac tacgacggcg acagctacct gaactggtac       120
cagcagaagc ccggccagcc ccccaagctg ctgatctacg acgccagcaa cctggtgagc       180
ggcgtgcccg ccggttcag cggcagcggc agcggcaccg acttcaccct gaccatcaac        240
cccgtggagg ccaacgacac cgccaactac tactgccagc agagcaccga ggaccctgg        300 accttcggcc agggcaccaa ggtggagatc aagcgg                                  336

<210> SEQ ID NO 3
<211> LENGTH: 124
<212> TYPE: PRT
<213> ORGANISM: Artificial sequence
<220> FEATURE:
<223> OTHER INFORMATION: huHD37 VH amino acid sequence

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met Asn Trp Val Arg Gln Ala Pro Gly Gln Gly Leu Glu Trp Met
        35                  40                  45

Gly Gln Ile Trp Pro Gly Asp Gly Asp Thr Asn Tyr Asn Gly Lys Phe
    50                  55                  60

Lys Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
            85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser
        115                 120
```

<210> SEQ ID NO 4
<211> LENGTH: 372
<212> TYPE: DNA
<213> ORGANISM: Artificial sequence
<220> FEATURE:
<223> OTHER INFORMATION: huHD37 VH  nucleotide sequence

<400> SEQUENCE: 4

```
caggtgcagc tggtgcagag cggcgccgag gtgaagaagc ccggcagcag cgtgaaggtg    60
agctgcaagg ccagcggcta caccttcagc agctactgga tgaactgggt gcggcaggcc   120
cccggccagg gcctggagtg gatgggccag atctggcccg gcgacggcga caccaactac   180
aacggcaagt tcaagggccg ggtgaccatc accgccgacg agagcaccag caccgcctac   240
atggagctga gcagcctgcg gagcgaggac accgccgtgt actactgcgc ccggcgggag   300
accaccaccg tgggccggta ctactacgca atggactact ggggccaggg caccaccgtg   360
accgtgagca gc                                                       372
```

<210> SEQ ID NO 5
<211> LENGTH: 124
<212> TYPE: PRT
<213> ORGANISM: Artificial sequence
<220> FEATURE:
<223> OTHER INFORMATION: 6B3 VH amino acid sequence

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Ile Asn Trp Val Arg Gln Ala Pro Gly Gln Gly Leu Glu Trp Met
        35                  40                  45

Gly Gln Ile Trp Pro Gly Asp Gly Glu Thr His Tyr Asn Gly Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser
        115                 120
```

<210> SEQ ID NO 6
<211> LENGTH: 372
<212> TYPE: DNA
<213> ORGANISM: Artificial sequence
<220> FEATURE:
<223> OTHER INFORMATION: 6B3 VH  nucleotide sequence

<400> SEQUENCE: 6

```
caggtgcagc tggtgcagag cggcgccgag gtgaagaagc ccggcagcag cgtgaaggtg    60
```

```
agctgcaagg ccagcggcta ccttcagc agctattgga taaactgggt gcggcaggcc    120
cccggccagg gcctggagtg gatgggccag atctggcccg gtgacggcga aacccactac    180
aacggcaagt tcaagggccg ggtgaccatc accgccgacg agagcaccag caccgcctac    240
atggagctga gcagcctgcg gagcgaggac accgccgtgt actactgcgc cggcggggag    300
accaccaccg tgggccggta ctactacgca atggactact ggggccaggg caccaccgtg    360
accgtgagca gc    372
```

```
<210> SEQ ID NO 7
<211> LENGTH: 112
<212> TYPE: PRT
<213> ORGANISM: Artificial sequence
<220> FEATURE:
<223> OTHER INFORMATION: 8E3 VL amino acid sequence

<400> SEQUENCE: 7

Asp Ile Val Leu Thr Gln Ser Pro Ala Ser Leu Ala Val Ser Pro Gly
1               5                   10                  15

Gln Arg Ala Thr Ile Thr Cys Lys Ala Ser His Ser Leu Asp Tyr Asp
            20                  25                  30

Gly Asp Asn Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Thr
                85                  90                  95

Glu Asp Pro Trp Thr Phe Gly Gln Gly Thr Lys Val Glu Ile Lys Arg
            100                 105                 110
```

```
<210> SEQ ID NO 8
<211> LENGTH: 336
<212> TYPE: DNA
<213> ORGANISM: Artificial sequence
<220> FEATURE:
<223> OTHER INFORMATION: 8E3 VL nucleotide sequence

<400> SEQUENCE: 8
gacatcgtgc tgacccagag ccccgccagc ctggccgtga gccccggcca gcgggccacc    60
atcacctgca aggccagcca tagcttggac tacgacggag acaactacct gaactggtac    120
cagcagaagc ccggccagcc ccccaagctg ctgatctacg acgccagcaa cctggtgagc    180
ggcgtgcccg ccggttcag cggcagcggc agcggcaccg acttcaccct gaccatcaac    240
cccgtggagg ccaacgacac cgccaactac tactgccagc agagcaccga ggacccctgg    300
accttcggcc agggcaccaa ggtggagatc aagcgg    336
```

```
<210> SEQ ID NO 9
<211> LENGTH: 5
<212> TYPE: PRT
<213> ORGANISM: Artificial sequence
<220> FEATURE:
<223> OTHER INFORMATION: murine antibody HD37 heavy chain CDR1

<400> SEQUENCE: 9

Ser Tyr Trp Met Asn
1               5
```

```
<210> SEQ ID NO 10
<211> LENGTH: 17
<212> TYPE: PRT
<213> ORGANISM: Artificial sequence
<220> FEATURE:
<223> OTHER INFORMATION: murine antibody HD37 heavy chain CDR2

<400> SEQUENCE: 10

Gln Ile Trp Pro Gly Asp Gly Asp Thr Asn Tyr Asn Gly Lys Phe Lys
1               5                   10                  15

Gly

<210> SEQ ID NO 11
<211> LENGTH: 15
<212> TYPE: PRT
<213> ORGANISM: Artificial sequence
<220> FEATURE:
<223> OTHER INFORMATION: murine antibody HD37 heavy chain CDR3

<400> SEQUENCE: 11

Arg Glu Thr Thr Thr Val Gly Arg Tyr Tyr Tyr Ala Met Asp Tyr
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: murine antibody HD37 light chain CDR1

<400> SEQUENCE: 12

Lys Ala Ser Gln Ser Val Asp Tyr Asp Gly Asp Ser Tyr Leu Asn
1               5                   10                  15

<210> SEQ ID NO 13
<211> LENGTH: 7
<212> TYPE: PRT
<213> ORGANISM: Artificial sequence
<220> FEATURE:
<223> OTHER INFORMATION: murine antibody HD37 light chain CDR2

<400> SEQUENCE: 13

Asp Ala Ser Asn Leu Val Ser
1               5

<210> SEQ ID NO 14
<211> LENGTH: 9
<212> TYPE: PRT
<213> ORGANISM: Artificial sequence
<220> FEATURE:
<223> OTHER INFORMATION: murine antibody HD37 light chain CDR3

<400> SEQUENCE: 14

Gln Gln Ser Thr Glu Asp Pro Trp Thr
1               5

<210> SEQ ID NO 15
<211> LENGTH: 5
<212> TYPE: PRT
<213> ORGANISM: Artificial sequence
<220> FEATURE:
<223> OTHER INFORMATION: variant 6B3 heavy chain CDR1

<400> SEQUENCE: 15

Ser Tyr Trp Ile Asn
1               5
```

```
<210> SEQ ID NO 16
<211> LENGTH: 17
<212> TYPE: PRT
<213> ORGANISM: Artificial sequence
<220> FEATURE:
<223> OTHER INFORMATION: variant 6B3 heavy chain CDR2

<400> SEQUENCE: 16

Gln Ile Trp Pro Gly Asp Gly Glu Thr His Tyr Asn Gly Lys Phe Lys
1               5                   10                  15
Gly

<210> SEQ ID NO 17
<211> LENGTH: 15
<212> TYPE: PRT
<213> ORGANISM: Artificial sequence
<220> FEATURE:
<223> OTHER INFORMATION: variant 8E3 light chain CDR1

<400> SEQUENCE: 17

Lys Ala Ser His Ser Leu Asp Tyr Asp Gly Asp Asn Tyr Leu Asn
1               5                   10                  15

<210> SEQ ID NO 18
<211> LENGTH: 556
<212> TYPE: PRT
<213> ORGANISM: Artificial sequence
<220> FEATURE:
<223> OTHER INFORMATION: human CD19 amino acid sequence

<400> SEQUENCE: 18

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
```

```
            210                 215                 220
Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                    245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                    325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                    405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                    485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
        530                 535                 540

Gly Gly Gly Gly Arg Met Gly Thr Trp Ser Thr Arg
545                 550                 555

<210> SEQ ID NO 19
<211> LENGTH: 112
<212> TYPE: PRT
<213> ORGANISM: Artificial sequence
<220> FEATURE:
<223> OTHER INFORMATION: 6B3 VL amino acid sequence

<400> SEQUENCE: 19

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
```

```
            20                  25                  30
Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110
```

<210> SEQ ID NO 20
<211> LENGTH: 124
<212> TYPE: PRT
<213> ORGANISM: Artificial sequence
<220> FEATURE:
<223> OTHER INFORMATION: 8E3 VH amino acid sequence

<400> SEQUENCE: 20

```
Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 21
<211> LENGTH: 251
<212> TYPE: PRT
<213> ORGANISM: Artificial sequence
<220> FEATURE:
<223> OTHER INFORMATION: amino acid sequence of scFv of huHD37

<400> SEQUENCE: 21

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Ser Tyr
                20                  25                  30

Trp Met Asn Trp Val Arg Gln Ala Pro Gly Gln Gly Leu Glu Trp Met
            35                  40                  45

Gly Gln Ile Trp Pro Gly Asp Gly Asp Thr Asn Tyr Asn Gly Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Gly Gly Gly Gly
        115                 120                 125

Ser Gly Gly Gly Gly Ser Gly Gly Gly Ser Asp Ile Val Leu Thr
    130                 135                 140

Gln Ser Pro Ala Ser Leu Ala Val Ser Pro Gly Gln Arg Ala Thr Ile
145                 150                 155                 160

Thr Cys Lys Ala Ser Gln Ser Val Asp Tyr Asp Gly Asp Ser Tyr Leu
                165                 170                 175

Asn Trp Tyr Gln Gln Lys Pro Gly Gln Pro Pro Lys Leu Leu Ile Tyr
            180                 185                 190

Asp Ala Ser Asn Leu Val Ser Gly Val Pro Ala Arg Phe Ser Gly Ser
        195                 200                 205

Gly Ser Gly Thr Asp Phe Thr Leu Thr Ile Asn Pro Val Glu Ala Asn
    210                 215                 220

Asp Thr Ala Asn Tyr Tyr Cys Gln Gln Ser Thr Glu Asp Pro Trp Thr
225                 230                 235                 240

Phe Gly Gln Gly Thr Lys Val Glu Ile Lys Arg
                245                 250
```

<210> SEQ ID NO 22
<211> LENGTH: 753
<212> TYPE: DNA
<213> ORGANISM: Artificial sequence
<220> FEATURE:
<223> OTHER INFORMATION: nucleotide sequence of scFv of huHD37

<400> SEQUENCE: 22

```
caggtgcagc tggtgcagag cggcgccgag gtgaagaagc ccggcagcag cgtgaaggtg      60
agctgcaagg ccagcggcta caccttcagc agctactgga tgaactgggt gcggcaggcc     120
cccggccagg gcctggagtg gatgggccag atctggcccg cgacggcga caccaactac      180
aacggcaagt tcaagggccg ggtgaccatc accgccgacg agagcaccag caccgcctac     240
atggagctga gcagcctgcg gagcgaggac accgccgtgt actactgcgc cggcggggag     300
accaccaccg tgggccggta ctactacgca atggactact ggggccaggg caccaccgtg     360
accgtgagca gcgtggagg cggttcaggc ggaggtggtt ctggcggtgg cggatcggac     420
atcgtgctga cccagagccc cgccagcctg gccgtgagcc ccggccagcg ggccaccatc     480
acctgcaagg ccagcagag cgtggactac gacggcgaca gctacctgaa ctggtaccag     540
cagaagcccg gccagccccc caagctgctg atctacgacg ccagcaacct ggtgagcggc     600
gtgcccgccc ggttcagcgg cagcggcagc ggcaccgact caccctgac catcaacccc      660
gtggaggcca acgacaccgc caactactac tgccagcaga gcaccgagga ccctggacc      720
ttcggccagg gcaccaaggt ggagatcaag cgg                                  753
```

<210> SEQ ID NO 23
<211> LENGTH: 21
<212> TYPE: PRT
<213> ORGANISM: Artificial sequence
<220> FEATURE:
<223> OTHER INFORMATION: CD8 signal peptide

<400> SEQUENCE: 23

```
Met Ala Leu Pro Val Thr Ala Leu Leu Leu Pro Leu Ala Leu Leu Leu
1               5                   10                  15
```

-continued

His Ala Ala Arg Pro
            20

<210> SEQ ID NO 24
<211> LENGTH: 63
<212> TYPE: DNA
<213> ORGANISM: Artificial sequence
<220> FEATURE:
<223> OTHER INFORMATION: nucleotide sequence of CD8 signal peptide

<400> SEQUENCE: 24
atggccttac cagtgaccgc cttgctcctg ccgctggcct tgctgctcca cgccgccagg    60
ccg                                                                  63

<210> SEQ ID NO 25
<211> LENGTH: 45
<212> TYPE: PRT
<213> ORGANISM: Artificial sequence
<220> FEATURE:
<223> OTHER INFORMATION: CD8 hinge

<400> SEQUENCE: 25

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 26
<211> LENGTH: 135
<212> TYPE: DNA
<213> ORGANISM: Artificial sequence
<220> FEATURE:
<223> OTHER INFORMATION: nucleotide sequence of CD8 hinge

<400> SEQUENCE: 26
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135

<210> SEQ ID NO 27
<211> LENGTH: 27
<212> TYPE: PRT
<213> ORGANISM: Artificial sequence
<220> FEATURE:
<223> OTHER INFORMATION: amino acid sequence of CD28 transmembrane
      region

<400> SEQUENCE: 27

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 28
<211> LENGTH: 81
<212> TYPE: DNA
<213> ORGANISM: Artificial sequence
<220> FEATURE:
<223> OTHER INFORMATION: nucleotide sequence of CD28 transmembrane
      region

<400> SEQUENCE: 28

```
ttttgggtgc tggtggtggt tggtggagtc ctggcttgct atagcttgct agtaacagtg    60
gcctttatta ttttctgggt g                                              81
```

<210> SEQ ID NO 29
<211> LENGTH: 41
<212> TYPE: PRT
<213> ORGANISM: Artificial sequence
<220> FEATURE:
<223> OTHER INFORMATION: amino acid sequence of CD28 intracellular
      region

<400> SEQUENCE: 29

```
Arg Ser Lys Arg Ser Arg Leu Leu His Ser Asp Tyr Met Asn Met Thr
1               5                  10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 30
<211> LENGTH: 123
<212> TYPE: DNA
<213> ORGANISM: Artificial sequence
<220> FEATURE:
<223> OTHER INFORMATION: nucleotide sequence of CD28 intracellular
      region

<400> SEQUENCE: 30

```
aggagtaaga ggagcaggct cctgcacagt gactacatga acatgactcc ccgccgcccc    60
gggccaaccc gcaagcatta ccagccctat gccccaccac gcgacttcgc agcctatcgc   120
tcc                                                                 123
```

<210> SEQ ID NO 31
<211> LENGTH: 113
<212> TYPE: PRT
<213> ORGANISM: Artificial sequence
<220> FEATURE:
<223> OTHER INFORMATION: amino acid sequence of CD3Z domain

<400> SEQUENCE: 31

```
Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 32
<211> LENGTH: 339
<212> TYPE: DNA

```
<213> ORGANISM: Artificial sequence
<220> FEATURE:
<223> OTHER INFORMATION: nucleotide sequence of CD3Z domain

<400> SEQUENCE: 32
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgcag agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg cccccctcgc                         339

<210> SEQ ID NO 33
<211> LENGTH: 21
<212> TYPE: PRT
<213> ORGANISM: Artificial sequence
<220> FEATURE:
<223> OTHER INFORMATION: amino acid sequence of CD8 transmembrane region

<400> SEQUENCE: 33

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 34
<211> LENGTH: 63
<212> TYPE: DNA
<213> ORGANISM: Artificial sequence
<220> FEATURE:
<223> OTHER INFORMATION: nucleotide sequence of CD8 transmembrane region

<400> SEQUENCE: 34
atctacatct gggcgccctt ggccgggact tgtgggggtcc ttctcctgtc actggttatc     60
acc                                                                   63

<210> SEQ ID NO 35
<211> LENGTH: 42
<212> TYPE: PRT
<213> ORGANISM: Artificial sequence
<220> FEATURE:
<223> OTHER INFORMATION: amino acid sequence of CD137 intracellular
      region

<400> SEQUENCE: 35

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 36
<211> LENGTH: 126
<212> TYPE: DNA
<213> ORGANISM: Artificial sequence
<220> FEATURE:
<223> OTHER INFORMATION: nucleotide sequence of CD137 intracellular
      region

<400> SEQUENCE: 36
```

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126
```

<210> SEQ ID NO 37
<211> LENGTH: 194
<212> TYPE: DNA
<213> ORGANISM: Artificial sequence
<220> FEATURE:
<223> OTHER INFORMATION: NFAT6 promoter
<400> SEQUENCE: 37

```
acgccttctg tatgaaacag ttttcctcc acgccttctg tatgaaacag ttttcctcc     60 acgccttctg tatgaaacag ttttcctcc gtcgaggaca attgacgcct tctgtatgaa   120 acagttttc ctccacgcct tctgtatgaa acagttttc ctccacgcct tctgtatgaa   180 acagttttc ctcc                                                     194
```

<210> SEQ ID NO 38
<211> LENGTH: 114
<212> TYPE: DNA
<213> ORGANISM: Artificial sequence
<220> FEATURE:
<223> OTHER INFORMATION: IL-2 mini promoter
<400> SEQUENCE: 38

```
caggagttga ggttactgtg agtagtgatt aaagagagtg atagggaact cttgaacaag    60
agatgcaatt tatactgtta attctggaaa aatattatgg gggtgtcaaa atgt         114
```

<210> SEQ ID NO 39
<211> LENGTH: 185
<212> TYPE: PRT
<213> ORGANISM: Artificial sequence
<220> FEATURE:
<223> OTHER INFORMATION: IFNb CDS amino acid sequence
<400> SEQUENCE: 39

```
Leu Val Ser Glu Val Thr Cys Lys Ser Val Asn Glu Val Lys Val Pro
1               5                   10                  15

Asp Phe His Ser Asp Tyr Gly Pro Gly Thr Val Thr Val Leu Leu Gly
            20                  25                  30

Leu Gln Val Met Gln Asn Pro Pro Ile Ile Ser Phe Gln Val Gln Thr
        35                  40                  45

Ala His Glu Phe Ser Pro Gly Glu Ile Phe Phe Leu Gln Phe Phe Phe
    50                  55                  60

Gln Asp Cys Leu Gln Met Val Tyr Leu Met Ile Asp Ile Ser Gln Glu
65                  70                  75                  80

Val Leu Asn Asn Ser Leu Ile Pro Ala Ser Ala Arg Ile Leu Ser Glu
                85                  90                  95

Asn Ser Lys Asp Val Leu Glu His Leu Ile Asp Gly Gln Cys Gly Val
            100                 105                 110

Leu Leu Leu Glu Leu Leu Gln Leu Asn Leu Leu Arg Asp Val Lys
        115                 120                 125

Val His Pro Val Leu Glu Ala Val Phe Lys Pro Ile Gln Leu Pro
    130                 135                 140

Gln Glu Leu Leu Thr Leu Lys Ile Ala Ala Ser Leu Glu Ser Lys Gln
145                 150                 155                 160

Val Val Ala His Gly Lys Ser Cys Ser Gly Glu Ala Gln Gln Glu Ser
```

```
            165                 170                 175
Asn Leu Glu Glu Thr Leu Val Gly His
        180                 185

<210> SEQ ID NO 40
<211> LENGTH: 564
<212> TYPE: DNA
<213> ORGANISM: Artificial sequence
<220> FEATURE:
<223> OTHER INFORMATION: IFNb CDS nucleotide sequence

<400> SEQUENCE: 40
ttagtttcgg aggtaacctg taagtctgtt aatgaagtaa aagttcctta ggatttccac      60
tctgactatg gtccaggcac agtgactgta ctccttggcc ttcaggtaat gcagaatcct    120
cccataatat cttttcaggt gcagactgct catgagtttt cccctggtga aatcttcttt    180
ctccagtttt tcttccagga ctgtcttcag atggtttatc tgatgataga cattagccag    240
gaggttctca acaatagtct cattccagcc agtgctagat gaatcttgtc tgaaaatagc    300
aaagatgttc tggagcatct catagatggt caatgcggcg tcctccttct ggaactgctg    360
cagctgctta atctcctcag ggatgtcaaa gttcatcctg tccttgaggc agtattcaag    420
cctcccattc aattgccaca ggagcttctg acactgaaaa ttgctgcttc tttgtaggaa    480
tccaagcaag ttgtagctca tggaaagagc tgtagtggag aagcacaaca ggagagcaat    540
ttggaggaga cacttgttgg tcat                                           564

<210> SEQ ID NO 41
<211> LENGTH: 51
<212> TYPE: DNA
<213> ORGANISM: Artificial sequence
<220> FEATURE:
<223> OTHER INFORMATION: PA2 nucleotide sequence

<400> SEQUENCE: 41
ctcacacaaa aaaccaacac acagatgtaa tgaaaataaa gatattttat t              51

<210> SEQ ID NO 42
<211> LENGTH: 15
<212> TYPE: DNA
<213> ORGANISM: Artificial sequence
<220> FEATURE:
<223> OTHER INFORMATION: linker nucleotide sequence

<400> SEQUENCE: 42
ggggsggggs ggggs                                                      15

<210> SEQ ID NO 43
<211> LENGTH: 26
<212> TYPE: DNA
<213> ORGANISM: Artificial sequence
<220> FEATURE:
<223> OTHER INFORMATION: Synthetic contruct
<220> FEATURE:
<221> NAME/KEY: misc_feature
<223> OTHER INFORMATION: LMF Primer

<400> SEQUENCE: 43
caggaaacag ctatgaccat gattac                                          26

<210> SEQ ID NO 44
<211> LENGTH: 73
<212> TYPE: DNA
<213> ORGANISM: Artificial sequence
```

```
<220> FEATURE:
<223> OTHER INFORMATION: Synthetic construct
<220> FEATURE:
<221> NAME/KEY: misc_feature
<223> OTHER INFORMATION: C37H1R Primer
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 44
cactccaggc cctggccggg ggcctgccgc acccamnmn nmnmnmnmnn mnngaaggtg     60
tagccgctgg cct                                                      73

<210> SEQ ID NO 45
<211> LENGTH: 77
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: C37H2F Primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t

<400> SEQUENCE: 45
ccggccaggg cctggagtgg atgggcnnka tcnnkcccnn knnkggcnnk accnnktaca     60
acggcaagtt caagggc                                                   77

<210> SEQ ID NO 46
```

<211> LENGTH: 30
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: FdR Primer

<400> SEQUENCE: 46
gacgttagta aatgaattttt ctgtatgagg                                    30

<210> SEQ ID NO 47
<211> LENGTH: 74
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: C37L1R Primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 47
ctggccgggc ttctgctggt accamnnmnn gtamnnmnnm nnmnnmnnmn nmnngctmnn     60
gctggccttg cagg                                                      74

<210> SEQ ID NO 48
<211> LENGTH: 80
<212> TYPE: DNA
<213> ORGANISM: Artificial sequence
<220> FEATURE:
<223> OTHER INFORMATION: Synthetic construct
<220> FEATURE:
<221> NAME/KEY: misc_feature

```
<223> OTHER INFORMATION: C37L2F Primer
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t

<400> SEQUENCE: 48
accagcagaa gcccggccag ccccccaagc tgctgatcta cnnknnkagc nnkctgnnka      60
gcggcgtgcc cgcccggttc                                                 80

<210> SEQ ID NO 49
<211> LENGTH: 111
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HD37 VL

<400> SEQUENCE: 49

Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
     50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110

<210> SEQ ID NO 50
<211> LENGTH: 99
<212> TYPE: PRT
<213> ORGANISM: Artificial sequence
<220> FEATURE:
<223> OTHER INFORMATION: Synthetic construct

<400> SEQUENCE: 50

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Ser Phe Leu
             20                  25                  30

Gly Ile Asn Leu Ile His Trp Tyr Gln Gln Lys Pro Gly Gln Pro Pro
         35                  40                  45

Lys Leu Leu Ile Tyr Gln Ala Ser Asn Lys Asp Thr Gly Val Pro Ala
     50                  55                  60
```

```
Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Leu Gln Ser Lys
                 85                  90                  95

Asn Phe Pro

<210> SEQ ID NO 51
<211> LENGTH: 111
<212> TYPE: PRT
<213> ORGANISM: Artificial sequence
<220> FEATURE:
<223> OTHER INFORMATION: Synthetic construct

<400> SEQUENCE: 51

Asp Ile Val Leu Thr Gln Ser Pro Ala Ser Leu Ala Val Ser Pro Gly
  1               5                  10                  15

Gln Arg Ala Thr Ile Thr Cys Arg Ala Ser Glu Ser Val Ser Phe Leu
                 20                  25                  30

Gly Ile Asn Leu Ile His Trp Tyr Gln Gln Lys Pro Gly Gln Pro Pro
                 35                  40                  45

Lys Leu Leu Ile Tyr Gln Ala Ser Asn Lys Asp Thr Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Leu Gln Ser Lys
                 85                  90                  95

Asn Phe Pro Trp Thr Phe Gly Gln Gly Thr Lys Val Glu Ile Lys
            100                 105                 110

<210> SEQ ID NO 52
<211> LENGTH: 111
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: huHD37

<400> SEQUENCE: 52

Asp Ile Val Leu Thr Gln Ser Pro Ala Ser Leu Ala Val Ser Pro Gly
  1               5                  10                  15

Gln Arg Ala Thr Ile Thr Cys Lys Ala Ser Gln Ser Val Asp Tyr Asp
                 20                  25                  30

Gly Asp Ser Tyr Leu Asn Trp Tyr Gln Gln Lys Pro Gly Gln Pro Pro
                 35                  40                  45

Lys Leu Leu Ile Tyr Asp Ala Ser Asn Leu Val Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln Gln Ser Thr
                 85                  90                  95

Glu Asp Pro Trp Thr Phe Gly Gln Gly Thr Lys Val Glu Ile Lys
            100                 105                 110

<210> SEQ ID NO 53
<211> LENGTH: 124
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<223> OTHER INFORMATION: HD37 VH

<400> SEQUENCE: 53

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
            115                 120

<210> SEQ ID NO 54
<211> LENGTH: 98
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: IGHV1-69*01

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 55
<211> LENGTH: 124
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: IGHV1-69*01/GHJ6*01
<220> FEATURE:
<221> NAME/KEY: misc_feature
<222> LOCATION: (99)..(112)
<223> OTHER INFORMATION: Xaa can be any naturally occurring amino acid
``` or may be absent

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Val Trp Gly Gln Gly Thr Thr Val Thr Val Ser Ser
            115                 120

<210> SEQ ID NO 56
<211> LENGTH: 124
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: huHD37 VH

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met Asn Trp Val Arg Gln Ala Pro Gly Gln Gly Leu Glu Trp Met
        35                  40                  45

Gly Gln Ile Trp Pro Gly Asp Gly Asp Thr Asn Tyr Asn Gly Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
            115                 120